US007053062B2

(12) United States Patent
Gregory et al.

(10) Patent No.: US 7,053,062 B2
(45) Date of Patent: *May 30, 2006

(54) COMPOSITIONS AND METHODS FOR INDUCING GENE EXPRESSION

(75) Inventors: Richard J. Gregory, Westford, MA (US); Karen Vincent, Arlington, MA (US)

(73) Assignee: Genzyme Corporation, Cambridge, MA (US)

( * ) Notice: Subject to any disclaimer, the term of this patent is extended or adjusted under 35 U.S.C. 154(b) by 494 days.

This patent is subject to a terminal disclaimer.

(21) Appl. No.: 10/190,394

(22) Filed: Jul. 3, 2002

(65) Prior Publication Data

US 2003/0018007 A1 Jan. 23, 2003

Related U.S. Application Data

(63) Continuation of application No. 09/579,897, filed on May 26, 2000, now Pat. No. 6,432,927, which is a continuation of application No. 09/133,612, filed as application No. PCT/US98/25753 on Dec. 4, 1998.

(60) Provisional application No. 60/067,546, filed on Dec. 4, 1997.

(51) Int. Cl.
*A61K 31/70* (2006.01)
*C12N 15/00* (2006.01)
*C12N 15/63* (2006.01)
*C07H 21/04* (2006.01)

(52) U.S. Cl. ............... 514/44; 435/320.1; 435/455; 536/23.4

(58) Field of Classification Search ............. 435/320.1, 435/455, 325; 424/93.2; 514/44
See application file for complete search history.

(56) References Cited

U.S. PATENT DOCUMENTS

| 5,612,318 A | 3/1997 | Weichselbaum et al. |
| 5,674,730 A | 10/1997 | Baim |
| 5,707,618 A | 1/1998 | Armentano |
| 5,834,306 A | 11/1998 | Webster |
| 6,087,166 A | 7/2000 | Baron et al. |
| 6,121,246 A | 9/2000 | Isner |
| 6,124,131 A | 9/2000 | Semenza |
| 6,133,027 A | 10/2000 | Yee et al. |

FOREIGN PATENT DOCUMENTS

| WO | WO 91/19784 | 12/1991 |
| WO | WO 96/26742 | 9/1996 |
| WO | WO 96/39426 | 12/1996 |
| WO | WO 98/31701 | 7/1998 |
| WO | WO 98/56936 | 12/1998 |

OTHER PUBLICATIONS

Anderson et al, Human gene therapy, Apr. 30, 1998, *Nature*, vol. 392, pp. 25-30.
Bacon et al., *Biochemical and Biophysical Research Communications* 249: 811-816 (1988), "Regulation of the Drosophila bHLH-PAS Protein Sima by Hypoxia: Functional Evidence for Homology with Mammalian HIF-A Alpha".
Banai et al., *Cardiovascular Res.* 28: 1176-1179 (1994).
Benjamin et al., *Proc. Natl. Acad. Sci. USA* 87: 6263-6267 (1990).
Blanchard et al., *Molecular and Cellular Biology* 12: 5373-5385 (1992).
Blau et al., *Molecular and Cellular Biology* 16: 2044-2055 (1996).
Bunn et al., *Physiological Rev.* 76: 839-885 (1996).
Chiu et al., Optimizing energy potentials of success in protein tertiary structure prediction, May 1998, Folding & Design, vol. 3, pp. 223-228.
Cress et al., *Science* 251: 87-90 (1991).
Croston et al., *Genes & Development* 6: 2270-2281 (1992).
Dachs et al., *Nature Medicine* 3: 515-520 (1997).
Dejgaard et al., *Journal of Molecular Biology* 236: 33-48 (1990).
Ema et al., *Proc. Natl. Acad. Sci., USA* 94: 4273-4278 (1997).
Feldman et al., *Cardiovascular Res.* 32: 194-207 (1996).
Finkel et al., *FASEB J.* 9: 843-851 (1995).
Fishman, *Trends Cardiovasc Med.* 5: 211-217 (1995), "Conditional Transgenics".
Fishman, *Circ. Res.*, 82: 837-844 (1988), "Timing Is Everything in Life—Conditional Transgene Expression in the Cardiovascular System".
Forsythe et al., *Molecular and Cellular Biology* 16: 4604-4613 (1996).
Gleadle and Ratcliffe., *Molecular Medicine Today*, 122-129 (Mar. 1988), "Hypoxia and the Regulation of Gene Expression".
Gu et al., *Gene Expression* 7: 205-213 (1998).
Guillemin et al., *Cell* 89: 9-12 (1997).
Gupta et al., *Nucleic Acids Research* 24: 2324-2330 (1996).

(Continued)

*Primary Examiner*—David Guzo
*Assistant Examiner*—Quang Nguyen
(74) *Attorney, Agent, or Firm*—Madge R. Kanter

(57) ABSTRACT

The present invention provides recombinant nucleic acid molecules encoding a chimeric transactivator protein including a DNA binding domain of a DNA binding protein and a protein domain capable of transcriptional activation. The present invention also provides recombinant viral and non-viral vectors that are able to infect and/or transfect and sustain expression of a biologically active chimeric transactivator proteins in mammalian cells. Also provided are host cell lines and non-human transgenic animals capable of expressing biologically active chimeric transactivator proteins. In another aspect, compositions and methods for treating or preventing ischemic damage associated with hypoxia-related disorders are provided.

24 Claims, 8 Drawing Sheets

OTHER PUBLICATIONS

Hashimoto et al., *Am. J. Physiol.* 267 (5 Part 1): H1948-H1954 (1994).
Henderson et al., *The Journal of Biological Chemistry* 264: 18142-18148 (1989), "Structure, Organization, and Expression of the Rat Cardiac Myosin Light Chain-2 Gene".
Huang et al., *The Journal of Biological Chemistry* 271: 32253-32259 (1996).
Huang et al., *Proc. Natl. Acad. Sci. USA* 95: 7987-7992 (1988), "Regulation of Hypoxia-Inducible Factor 1 Alpha is Mediated by an O2-Dependent Degradation Domain Via the Ubiquitin-Proteasome Pathway".
Jiang et al., *The Journal of Biological Chemistry* 271: 17771-17778 (1996).
Jiang et al., *The Journal of Biological Chemistry* 272: 19253-19260 (1997).
Kadonaga et al., *Cell* 51: 1079-1090 (1987), "Isolation of cDNA Encoding Transcription Factor Sp1 and Functional Analysis of the DNA Binding Domain."
Karck et al., *Ann. Thorac. Surg.* 59: 699-706 (1995).
Lee et al., *Nature* 325: 368-372 (1987), "Activation of Transcription by Two Factors that Bind Promoter and Enhancer Sequences of the Human Metallothionein Gene and SV40".
Levy et al., *The Journal of Biological Chemistry* 270: 13333-13340 (1995).
Li et al., *The Journal of Biological Chemistry* 271: 21262-21267 (1996).
Li et al., *Ann Thorac Surg.* 62: 654-661 (1996), "Cardiomyocyte Transplantation Improves Heart Function".
Maltepe et al., *Nature* 386: 403-407 (1997).
Mastrangelo et al., Gene Therapy for Human Cancer: An Essay for Clinicians, Feb. 1996, Seminars in Oncology, vol. 23, No. 1, pp. 4-21.
Meng et al., Tumor Supperssor Genes as Targets for Cancer Gene Therapy, 1999, Gene Therapy of Cancer, Chapter 1, pp. 3-20.
Mermod et al., *Cell* 58: 741-753 (1989), "The Proline-Rich Transcriptional Activator of CTF/NF-I is Distinct from the Replication and DNA Binding Domain".
Neuman et al., *Gene* 173: 163-169 (1996), "Structure and Partical Genomic Sequence of the Human E2F1 Gene".
Ngo et al., Computational Complexity, Protein Structure Prediction, and the Levinthal Paradox, 1994, Birkhauaer Boston, pp. 491-495.
Norris et al., *The Journal of Biological Chemistry* 270: 23774-23779 (1995).
Pfeifer et al., *Cell* 56: 291-301 (1989), "Functional Dissection and Sequence of Yeast HAP1 Activator".
Pinkham et al., *Molecular and Cellular Biology* 7: 578-585 (1987), "Sequence and Nuclear Localization of the *Saccharomyces cerevisiae* HAP2 Protein, a Transcriptional Activator".
Pollack and Gilman, *Proc. Natl. Acad. Sci USA* 94: 13388-13389 (1997), "Transcriptional Activation: Is it Rocket Science?".
Ptashne, *Nature* 386: 569-577 (1997).
Ptashne, *Nature Medicine* 3: 1069-1072 (1997).
Ptashne, *Nature* 335: 683-689 (1988).
Pugh et al., *The Journal of Biological Chemistry* 272: 11205-11214 (1997).
Rabindran et al., *Proc. Natl. Acad. Sci. USA* 88: 6906-6910 (1991), "Molecular Cloning and Expression of a Human Heatshock Factor, HSF1".
Regier et al., *Proc. Natl. Acad. Sci. USA* 90: 883-887 (1993).
Rinsch et al., *Human Gene Therapy* 8: 1881-1889 (1997).
Ruoquain-Shen et al., *Molecular and Cellular Biology* 11: 1676-1685 (1991), "Tissue-Specific Transcription of the Cardiac Myosin Light-Chain 2 Gene is Regulated by an Upstream Repressor Element".
Schmitz and Baeuerle, *The EMBO Journal* 10: 3805-3817 (1991), "The p65 subunit is Responsible for the Strong Transcription Activating Potential of NF-kappaB".
Schmitz et al., *The Journal of Biological Chemistry* 269: 25613-25620 (1994), "Structural and Functional Analysis of the NF-kappaB p65 Terminus".
Schmitz et al., *The Journal of Biological Chemistry* 270: 15576-15584 (1985), "Transactivation Domain 2 (TA2) of p65 NF-kappaB".
Semenza et al., *The Journal of Biological Chemistry* 269: 23757-23763 (1994).
Semenza et al., *Kidney International* 51: 553-555 (1997).
Sengstag and Hinnen, *Nucleic Acids Research* 15: 233-246 (1987), "The sequence of the *Saccharomyces cerevisiae* Gene PHO2 Codes for a Regulatory Protein with Unusual Aminoacid Composition".
Shyu et al., *Circulation* 98: Abstract 342 (1998).
Simmen et al., *Journal of Virology* 71: 3886-3894 (1997).
Subramaniam et al., *The Journal of Biological Chemistry* 266: 24613-24620 (1991), "Tissue-specific Regulation of the Alpha-Myosin Heavy Chain Gene Promoter in Transgenic Mice*".
Suzuki et al., *Molecular and Cellular Biology* 8: 4991-4999 (1988), "GAL11 Protein, an Auxilliary Transcription Activator for Genes Encoding Galactose-Metabolizing Enzymes in *Saccharomyces cerevisiae*".
Tait et al., Ovarian Cancer BRCA1 Gene Therapy: Phase I and II Trial Differences in Immune Response and Vector Stability, Jul. 14, 1999, Clinical Cancer Research, vol. 5, pp. 1708-1714.
Tian et al., *Genes & Development* 11: 72-82 (1996).
Triezengerg, *Genetics and Development* 5: 190-196 (1995), "Structure and Function of Transcriptional Activation Domains".
Verma et al., Gene therapy-promises, problems, and propects, Sep. 18, 1997, Nature, vol. 389, pp. 239-242.
Vincent et al., Anglogenesis and Vascular Remodeling (1998).
Wang et al., *The Journal of Biological Chemistry* 270: 1230-1237 (1995).
Wang et al., *Proc. Natl. Acad. Sci. USA* 92: 5510-5514 (1995).
Wang et al., *Proc. Natl. Acad. Sci. USA* 90: 4304-4308 (1993).
Wang et al., *Journal of Biological Chemistry* 268: 21513-21518 (1993).
Weiner et al., *Biochemical and Biophysical Research Communications* 225: 485-488 (1996).
Wood et al., *The Journal of Biological Chemistry* 271: 15117-15123 (1996).
Wu et al., *Molecular and Cellular Biology* 14: 3484-3493 (1994).

COMPOSITIONS AND METHODS FOR INDUCING GENE EXPRESSION

This application is a continuation of U.S. Ser. No. 09/579,897, filed May 26, 2000, now issued as U.S. Pat. No. 6,432,927, which is a continuation of PCT patent application PCT/US98/25753, filed Dec. 4, 1998, which is a continuation-in-part of U.S. Ser. No. 09/133,612, filed Aug. 13, 1998 now abandoned, which claims priority under 35 U.S.C. § 119(e) to provisional application 60/067,546, filed Dec. 4, 1997.

BACKGROUND OF THE INVENTION

Ischemic heart disease occurs when the heart muscle does not receive an adequate blood supply and is thus deprived of necessary levels of oxygen and nutrients. Ischemia is commonly a result of atherosclerosis which causes blockages in the coronary arteries that provide blood flow to the heart muscle.

Ischemic heart disease can result in certain adaptive responses within the heart which are likely to be beneficial. Among these responses are: 1) increased expression of angiogenic growth factors and their receptors, leading to the formation of collateral circulation around blocked coronary arteries; 2) increased expression of glycolytic enzymes as a means to activate a metabolic pathway which does not require $O_2$; and 3) expression of heat shock proteins which can protect the ischemic tissue from death.

At least some of these responses appear to be regulated by a complex oxygen sensing mechanism which eventually leads to the activation of transcription factors which control the expression of critical genes involved in this adaptation. Because this altered gene expression occurs only in response to hypoxia, which usually only occurs when a strain such as exercise is placed upon the diseased heart, cardiac patients do not usually receive much benefit from this endogenous compensatory mechanism. As a result, a number of conventional therapies attempt to supplement the natural therapeutic responses of the heart to ischemia.

For example, such treatments include pharmacological therapies, coronary artery bypass surgery and percutaneous revascularization using techniques such as balloon angioplasty. Standard pharmacological therapy is predicated on strategies that involve either increasing blood supply to the heart muscle or decreasing the demand of the heart muscle for oxygen and nutrients.

Increased blood supply to the myocardium is achieved by agents such as calcium channel blockers or nitroglycerin. These agents are thought to increase the diameter of diseased arteries by causing relaxation of the smooth muscle in the arterial walls. Decreased demand of the heart muscle for oxygen and nutrients is accomplished either by agents that decrease the hemodynamic load on the heart, such as arterial vasodilators, or those that decrease the contractile response of the heart to a given hemodynamic load, such as beta-adrenergic receptor antagonists.

Surgical treatment of ischemic heart disease is based on the bypass of diseased arterial segments with strategically placed bypass grafts (usually saphenous vein or internal mammary artery grafts). Percutaneous revascularization is based on the use of catheters to reduce the narrowing in diseased coronary arteries. All of these strategies are used to decrease the number of, or to eradicate ischemic episodes, but all have various limitations.

More recently, delivery of angiogenic factors or heat shock proteins via protein or gene therapy has been proposed to further augment the heart's natural response to ischemia. Indeed, various publications have discussed the uses of gene transfer for the treatment or prevention heart disease. See, for example, Mazur et al., "Coronary Restenosis and Gene Therapy", *Molecular and Cellular Pharmacology* 21:104–111 (1994); French, B. A. "Gene Transfer and Cardiovascular Disorders" *Herz.* 18(4):222–229 (1993); Williams, "Prospects for Gene Therapy of Ischemic Heart Disease", *Am. J. Med. Sci.* 306:129–136 (1993); Schneider and French "The Advent of Adenovirus: Gene Therapy for Cardiovascular Disease" *Circulation* 88:1937–42 (1993). International Patent Application No. PCT/US93/11133, entitled "Adenovirus-Mediated Gene Transfer to Cardiac and Vascular Smooth Muscle" reporting the use of adenovirus-mediated gene transfer for regulating function in cardiac vascular smooth muscle.

Accordingly, there exists a need in the art for compositions and methods for inducing the expression of beneficial hypoxia-inducible genes in ischemia-associated cells. Additionally, there exists a need for new vector compositions that allow efficient expression of a range of potentially beneficial genes that are activated by the sustained direct expression of a biologically active mammalian transcription factor. The present invention satisfies these needs and provides related advantages as well.

SUMMARY OF THE INVENTION

The present invention provides recombinant nucleic acid molecules encoding a chimeric transactivator comprising a DNA binding domain of a DNA binding protein wherein the DNA binding protein is a mammalian hypoxia-inducible factor protein, and a functional transcriptional activator domain of a transcriptional activator protein.

Accordingly, in making the invention, we sought to exploit the adaptive response to hypoxia as an alternative approach for the treatment of ischemia associated with vascular disease. We considered that administration of a modified HIF-1α transcription factor via gene therapy might induce expression of a panel of potentially beneficial genes and ultimately lead to the neovascularization of ischemic tissues. We have created a constitutively active form of HIF-1α consisting of the DNA-binding and dimerization domains from HIF-1α and the transactivation domain from herpes simplex virus VP16 protein. Among the possible target genes for this modified transcription factor is VEGF, an endothelial cell-specific mitogen and potent stimulator of angiogenesis.

In vitro analyses of an HIF-1α/VP16 hybrid transcription factor of the invention demonstrated that activation of luciferase reporter constructs under the transcriptional control of either the VEGF or EPO promoters as well as up-regulation of endogenous VEGF gene expression in HeLa and C6 cells was independent of induction. Experiments were performed in a rabbit hindlimb ischemia model to test the hypothesis that exogenous administration of a plasmid encoding HIF-1α/VP16 could enhance collateral vessel formation and also to compare the potency of HIF-1α/VP16 with that of VEGF as an angiogenic therapy. Results of these studies suggest that administration of DNA encoding a transcription factor may represent a viable treatment strategy for tissue ischemia.

The present invention also provides recombinant viral and non-viral vectors that are able to infect and/or transfect and sustain expression of a biologically active chimeric human-viral transactivator protein in mammalian cells.

The present invention further provides a recombinant plasmid vector (pcDNA3/HIF/VP16/Af12).

In another embodiment, the present invention provides a recombinant plasmid expression vector (pcDNA3/HIF/VP16/RI).

In yet another embodiment, the present invention provides mammalian cells and cell lines transfected with pcDNA3/HIF/VP16/Af12 or pcDNA3/HIF/VP16/RI.

In still yet another embodiment, the present invention provides recombinant mammalian cell lines able to express biologically active chimeric human-viral transactivator protein at sustained levels.

The present invention also provides recombinant mammalian host cell lines able to express and secrete biologically active chimeric human-viral transactivator protein at sustained levels.

In another embodiment, the present invention provides a fusion protein comprising a DNA binding domain of a DNA binding protein wherein the DNA binding protein is the mammalian hypoxia-inducible factor 1α (HIF-1α) protein at the amino terminus, and a functional transcriptional activator domain of a transcriptional activator protein, wherein said transcriptional activator protein is HSV VP16 at the carboxy terminus.

The present invention further provides a non-human transgenic mammal expressing recombinant DNA encoding a chimeric transactivator comprising a DNA binding domain of a DNA binding protein wherein said DNA binding protein is the mammalian hypoxia-inducible factor 1α (HIF-1α) protein, and a functional transcriptional activator domain of a transcriptional activator protein, wherein said transcriptional activator protein is HSV VP16.

In yet another embodiment, the present invention provides a method for increasing expression of hypoxia-inducible genes.

In still yet another embodiment, the present invention provides a method for providing sustained expression of biologically active HIF-1α under normoxic conditions.

The present invention also provides a method for treating/preventing/modulating hypoxia-associated tissue damage in a subject.

The present invention further provides a method for providing biologically active chimeric human-viral transactivator protein to the cells of an individual comprising introducing into the cells of an individual an amount of pcDNA3/HIF/VP16/RI or pcDNA3/HIF/VP16/Af12 effective to transfect and sustain expression of biologically active chimeric human-viral transactivator protein in the cells of the individual.

Other features and advantages of the present invention will be apparent from the following detailed description as well as from the claims.

All patent applications, patents, and literature references cited in this specification are hereby incorporated by reference in their entirety. In case of conflict or inconsistency, the present description, including definitions, will control.

DETAILED DESCRIPTION OF THE INVENTION

Figure 1:
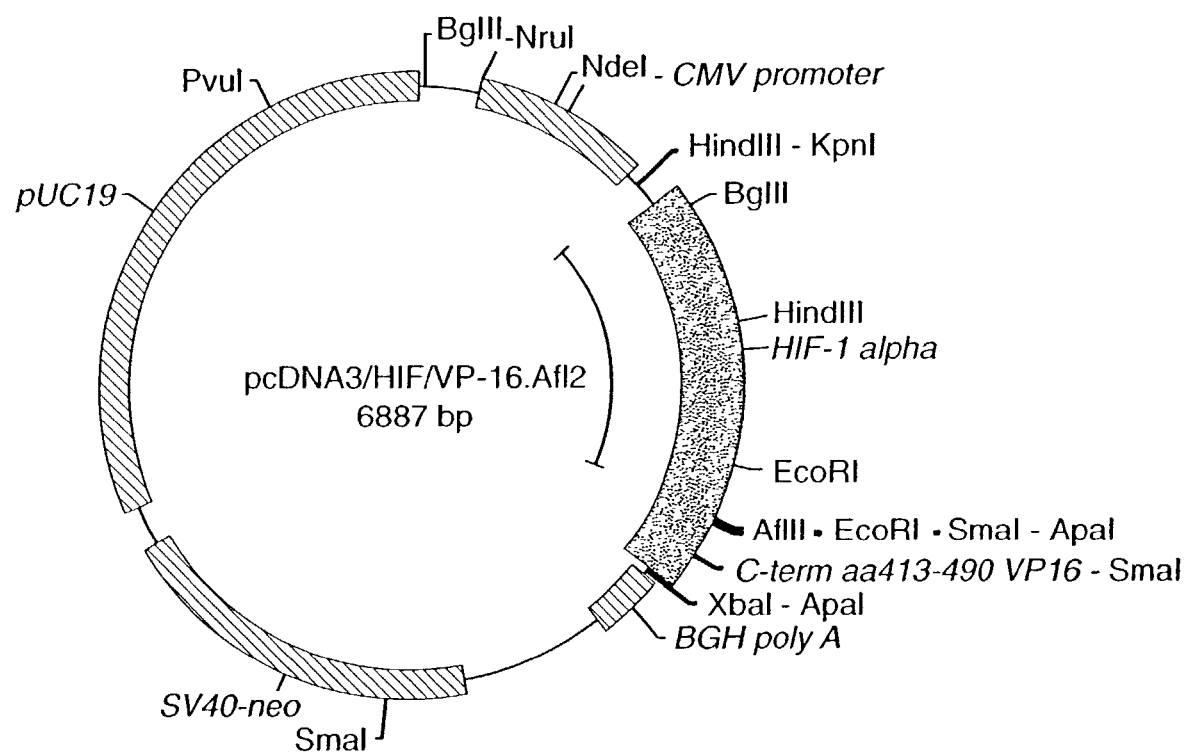
FIG. 1 shows a restriction map of hybrid construct pcDNA3/HIF/VP16/Af12.

Hypoxia (a state in which $O_2$ demand exceeds supply) is a powerful modulator of gene expression. The physiologic response to hypoxia involves enhanced erythropoiesis (Jelkman, Physiol. Rev. 72:449–489 (1992)), neovascularization in ischemic tissues (White et al., Circ. Res. 71:1490–1500 (1992)) and a switch to glycolysis-based metabolism (Wolfe et al., Eur. J. Biochem. 135:405–412 (1983)). These adaptive responses either increase $O_2$ delivery or activate alternate metabolic pathways that do not require $O_2$. The gene products involved in these processes, include, for example: (i) EPO, encoding erythropoietin, the primary regulator of erythropoiesis and thus a major determinant of blood $O_2$-carrying capacity (Jiang et al., J. Biol. Chem. 271(30): 17771–78 (1996); (ii) VEGF, encoding vascular endothelial growth factor, the primary regulator of angiogenesis and thus a major determinant of tissue perfusion (Levy et al., J. Biol. Chem. 270:13333 (1995); Liu et al., Circ. Res. 77:638 (1995); Forsythe et al., Mol. Cell. Biol. 16:4604 (1996)); (iii) ALDA, ENO1, LDHA, PFKL, and PGK1, encoding the glycolytic enzymes aldolase A, enolase 1, lactate dehydrogenase A, phosphofructokinase L, and phosphoglycerate kinase 1, respectively, which provide a metabolic pathway for ATP generation in the absence of $O_2$ (Firth et al., Proc. Natl. Acad. Sci., USA 91:6496 (1994); Firth et al., J. Biol. Chem. 270:21021 (1995); Semenza et al., J. Biol. Chem. 269:23757 (1994)); (iv) HO1 and iNOS, encoding heme oxygenase 1 and inducible nitric oxide synthase, which are responsible for the synthesis of the vasoactive molecules carbon monoxide and nitric oxide, respectively (Lee et al., J. Biol. Chem. 272:5375; Melillo et al. J. Exp. Med. 182: 1683 (1995)).

An important mediator of these responses is the interaction of a transcriptional complex comprising a DNA binding, hypoxia inducible factor protein, with its cognate DNA recognition site, a hypoxia-responsive element (HRE) located within the promoter/enhancer elements of hypoxia-inducible genes. HREs consist of an hypoxia inducible factor protein binding site (that contains the core sequence 5'-CGTG-3') as well as additional DNA sequences that are required for function, which in some elements includes a second binding site.

HIF-1 is a heterodimeric protein composed of two subunits: (i) a constitutively expressed beta (β) subunit (shared by other related transcription factors) and (ii) an alpha (α) subunit (see, e.g., WO 96/39426, International Application No. PCT/US96/10251 describing the recent affinity purification and molecular cloning of HIF-1α) whose accumulation is regulated by a post-translational mechanism such that high levels of the alpha subunit can only be detected during hypoxic conditions. Both subunits are members of the basic helix-loop-helix (bHLH)-PAS family of transcription factors. These domains regulate DNA binding and dimerization. The transactivation domain is thought to reside in the C-terminus of the protein.

Whereas, HIF-1β (ARNT) is expressed constitutively at a high level, accumulation of HIF-1α in the cell is sensitive to $O_2$ concentration such that high levels are detected only during hypoxia. This observation has led to a proposed mechanism for target gene activation whereby $O_2$ concentration is detected by a sensor protein and through a complex signaling mechanism leads to stabilization of the HIF-1α subunit. HIF-1α is then available to complex with HIF-1β and bind selectively to HRE sites in the promoter/enhancer of the target gene(s). Regions of the HIF-1α protein involved in conferring this response are thought to coincide with regions involved in transactivation.

Induction of HIF-1 activity in response to hypoxia is thought to occur via stabilization of the HIF-1α protein. Regions of HIF-1α involved in this response have been localized to the C-terminus of the protein and overlap the transactivation domain. For example, Jiang et al., *J. Biol. Chem.* 271(30):17771–78 (1996) showed that HIF-1α truncated at amino acid 390 lost transactivation activity but retained the ability to bind DNA and showed high levels of protein under both normoxic and hypoxic conditions. This result suggested that the transactivation domain as well as the region conferring instability with normoxia reside in the C-terminal half of the protein. Pugh et al., *J. Biol. Chem.* 272(17):11205–14 (1997) have further localized the regions involved to two areas, amino acids 549–582 and 775–826.

In one embodiment, this invention provides nucleic acid molecules encoding biologically active chimeric transactivator proteins comprising a domain of the HIF-1α protein sufficient for DNA binding and dimerization with HIF-1β (ARNT) and a protein domain capable of transcriptional activation.

In another embodiment, a related DNA binding, hypoxia inducible factor protein is EPAS1. EPAS1 is a PAS domain transcription factor termed endothelial PAS-1. Tian et al., *Genes Dev.* 11:72 (1997). EPAS1 shares 48% identity with HIF-1α and lesser similarity with other members of bHLH/PAS domain family of transcription factors (EPAS1 human sequence GenBank Acc. No. U81984; mouse sequence GenBank Ace. No. U81983). Like HIF-1α, EPAS1 binds to and activates transcription from a DNA element originally isolated from the EPO gene and containing the HRE core sequence. EPAS1 also forms a heterodimeric complex with ARNT prior to transcriptional activation of target genes.

Human and murine EPAS1 share extensive primary amino acid sequence identity with HIF-1α (48%). Sequence conservation between the two proteins is highest in the bHLH (85%), PAS-A (68%), and PAS-B (73%) regions. A second region of sequence identity occurs at the extreme C termini of the EPAS1 and HIF-1α proteins. This conserved region in mHIF-1α has been shown to contain a hypoxia response domain (Li et al., *J. Biol. Chem.* 271(35):21262–67 (1996)). The high degree of sequence similarity between EPAS1 and HIF-1α suggests that they share a common physiological function. Hypoxic conditions stimulate the ability of HIF-1α to trans-activate a target gene containing the HRE core sequence. The activity of EPAS1 is also enhanced in cells grown under hypoxic conditions, suggesting that it may be subject to the same regulatory influences as HIF-1α.

In yet another embodiment of the present invention the transcription factor, DNA binding, hypoxia inducible factor protein is HLF. HLF is a bHLH-PAS protein termed HIF-1α-like factor. Ema et al., *Proc. Natl. Acad. Sci., USA* 94:4273 (1997). HLF is a novel polypeptide of 874 amino acids with a calculated molecular mass of 97 kDa (GenBank Accession No. D89787). Sequence comparison revealed that the amino acid sequence has a striking similarity to that of HIF-1α in the amino-terminal half (aa1–344) including bHLH (83.9%) and PAS (66.5%) motifs followed by a sequence with a moderate similarity (36.4%, aa 345–559). While most of the sequence in the C-terminal half was variable between this protein and HIF-1α, a small portion (63%, aa 824–874) of noticeable sequence similarity was found in the very C terminus. That basic amino acids of the bHLH region involved in DNA recognition are completely conserved among HLF and HIF-1α, suggests that these factors recognize very similar, if not identical, regulatory DNA sequences. Experiments showed that both HLF and HIF-1α bound the VEGF and EPO HRE sequences in association with ARNT with a similar affinity.

In another embodiment, the chimeric transactivator proteins of this invention comprise a domain of a non-mammalian hypoxia inducible factor protein. As will be recognized by the skilled artisan, the adaptive response to hypoxia is likely to have been highly conserved throughout evolution. Accordingly, hypoxia inducible factor proteins would be expected to occur in a wide variety of species including non-mammalian vertebrates and non-vertebrates such as insects. See, for example, Bacon et al., *Biochem. Biophys. Res. Comm.*, 249:811–816 (1998), which reports the functional similarity between the Sima basic-helix-loop-helix PAS protein from *Drosophila* and the mammalian HIF-1α protein.

Nucleic acid and amino acid sequences for non-mammalian hypoxia inducible factor proteins may be obtained by the skilled artisan by a variety of techniques, for example by cross-hybridization or amplification using all or a portion of the sequences referred to herein. Once the sequence encoding a candidate hypoxia inducible factor protein has been determined, the localization of portions of the protein sufficient to bind to HREs and dimerize with HIF-1β may be determined using, e.g., the same types of techniques used to determine the location of those domains within the human HIF-1α protein. Relevant domains of non-mammalian hypoxia inducible factor proteins useful in the compositions and methods of this invention may also be produced synthetically or by site-directed manipulations of the DNA encoding known mammalian hypoxia inducible factor proteins. It is also expected that the sequence motifs in common among various mammalian and non-mammalian hypoxia inducible factor proteins will suggest consensus sequences that, while perhaps not occurring naturally in any species, would nevertheless produce domains useful in the methods and compositions of this invention. All that is required in order to substitute such non-mammalian hypoxia inducible factor protein domains for the human HIF-1α protein domains exemplified herein is that they be able to bind to HREs and dimerize with HIF-1β (ARNT).

Accordingly, it is proposed to modify the hypoxia inducible factor protein by removing the C-terminal (transactivation)domain and replacing it with a strong transactivator sequence. This modification should not alter its ability to dimerize with the β/ARNT subunit or bind to specific DNA sequences (e.g., HREs) but could convert the hypoxia inducible factor protein into a constitutive inducer of potentially therapeutic genes (for example, VEGF, EPO, phosphoglycerate kinase, and the like).

Replacement of the C terminal (or transactivation) region of the hypoxia inducible factor protein with a strong transactivation domain from a transcriptional activator protein such as, for example, Herpes Simplex Virus (HSV) VP16 or yeast transcription factors GAL4 and GCN4, is designed to stabilize the protein under normoxic conditions and provide strong, constitutive, transcriptional activation. Administration of this protein to the cells of a subject via gene therapy should be an effective treatment or prophylactic for chronic ischemia due to coronary artery disease, peripheral vascular disease as well as ischemic disease of the limb.

In the present application, of interest is the ability of hypoxia inducible factor proteins, for example, HIF-1α, EPAS1 and HLF to induce expression of hypoxia-inducible genes such as, for example VEGF and the like, resulting in the amelioration of symptoms through promotion of collateral blood vessel growth.

For example, although the HIF-1α subunit is unstable during normoxic conditions, overexpression of this subunit in cultured cells under normal oxygen levels is capable of inducing expression of genes normally induced by hypoxia. This suggests that a useful gene therapy strategy might be to express high levels of the HIF-1α subunit in ischemic heart in vivo using a recombinant plasmid or viral vector. An alternative strategy would be to modify the HIF-1α subunit such that it no longer is destabilized by normoxic conditions and would therefore be more potent, particularly when the patient being treated is not actually ischemic.

To stabilize the hypoxia inducible factor protein under normoxic conditions and to provide strong, constitutive transcriptional activation, a hybrid/chimeric fusion protein consisting of the DNA-binding and dimerization domains from HIF-1α and the transactivation domain from Herpes Simplex Virus (HSV) VP16 protein was constructed. Administration of this hybrid/chimera to the cells of a subject via gene therapy will theoretically induce the expression of genes normally up-regulated in response to hypoxia (i.e., VEGF and the like).

Alternative biologically active chimeric transactivator proteins, such as a protein comprising the DNA binding and dimerization domain from HIF-1α and the transactivation domain from the human NFκB protein, are expected to produce similar results.

"Hypoxia" means the state in which $O_2$ demand exceeds supply.

"Hypoxia-inducible genes" means genes containing one or more hypoxia responsive elements (HREs; binding sites) within sequences mediating transcriptional activation in hypoxic cells.

Hypoxia inducible factor means a DNA binding protein/transcription factor the expression of which is upregulated under hypoxic conditions, that recognizes and binds to a hypoxia responsive element core sequence within a gene and thereby activates such gene.

Hypoxia-associated disorders include, for example, ischemic heart disease, peripheral vascular disease, ischemic disease of the limb, and the like.

The term "nucleic acids" (also referred to as polynucleotides) encompasses RNA as well as single and double-stranded DNA, cDNA and oligonucleotides.

Nucleic acids also encompass isolated nucleic acid sequences, including sense and antisense oligonucleotide sequences, e.g., derived from the HIF-1α, EPAS1, or the HLF sequences. HIF-1α, EPAS1-, or HLF-derived sequences may also be associated with heterologous sequences, including promoters, enhancers, response elements, signal sequences, polyadenylation sequences, and the like. As used herein, the phrase "isolated" means a polynucleotide that is in a form that does not occur in nature. One means of isolating polynucleotides is to probe a human tissue-specific library with a natural or artificially designed DNA probe using methods well known in the art. DNA probes derived from the human HIF-1α gene, EPAS1, or the HLF gene are particularly useful for this purpose. DNA and cDNA molecules that encode invention polypeptides can be used to obtain complementary genomic DNA, cDNA or RNA from human, mammalian, or other animal sources, or to isolate related cDNA or genomic clones by the screening of cDNA or genomic libraries, by methods described in more detail below.

Furthermore, the nucleic acids can be modified to alter stability, solubility, binding affinity, and specificity. For example, invention-derived sequences can further include nuclease-resistant phosphorothioate, phosphoroamidate, and methylphosphonate derivatives, as well as "protein nucleic acid" (PNA) formed by conjugating bases to an amino acid backbone as described in Nielsen et al., *Science*, 254:1497, (1991). The nucleic acid may be derivatized by linkage of the α-anomer nucleotide, or by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

In general, nucleic acid manipulations according to the present invention use methods that are well known in the art, as disclosed in, for example, Sambrook et al., *Molecular Cloning, A Laboratory Manual 2d Ed.* (Cold Spring Harbor, N.Y., 1989), or Ausubel et al., *Current Protocols in Molecular Biology* (Greene Assoc., Wiley Interscience, NY, N.Y., 1992).

This invention also encompasses nucleic acids which differ from the nucleic acids encoding a human HIF-1α, EPAS1, or HLF, but which have the same phenotype, i.e., encode substantially the same amino acid sequence, respectively. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same or substantially the same protein product(s) as the nucleic acids disclosed herein. In particular, functionally equivalent nucleic acids encode proteins that are the same as those disclosed herein or that have conservative amino acid variations. For example, conservative variations include substitution of a non-polar residue with another non-polar residue, or substitution of a charged residue with a similarly charged residue. These variations include those recognized by skilled artisans as those that do not substantially alter the tertiary structure of the protein.

A structural gene is that portion of a gene comprising a DNA segment encoding a protein, polypeptide or a portion thereof, and excluding the 5' sequence which drives the initiation of transcription. The structural gene may be one which is normally found in the cell or one which is not normally found in the cellular location wherein it is introduced, in which case it is termed a heterologous gene. A heterologous gene may be derived in whole or in part from any source know to the art, including a bacterial genome or episome, eukaryotic, nuclear or plasmid DNA, cDNA, vital DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions. The structural gene may be a composite of segments derived from a plurality of sources, naturally occurring or synthetic. The structural gene may also encode a fusion protein. It is contemplated that the introduction of recombinant DNA molecules containing the structural gene/transactivator complex will include constructions wherein the structural gene and the transactivator are each derived from different sources or species.

Eukaryotic transcription factors are often composed of separate and independent DNA binding and transcriptional activator domains (Mitchell and Tjian, *Science* 245:371–378 (1989)). The independence of the domains has allowed for the creation of functional fusion proteins consisting of the DNA binding and activating domains of heterologous proteins. Chimeric eukaryotic regulatory proteins, consisting of the lexA DNA binding protein and the activation domain of the yeast transcription factor, GAL4, were constructed by Brent and Ptashne (*Nature* 312:612–615 (1985)). The use of fusion proteins has identified several types of protein domains which act as transcriptional activators. These domains have little amino acid similarity but often are characterized as being either highly acidic (as in the case of GAL4 and GNC4), glutamine-rich (as in the case of Sp1), or proline-rich (as in the case of NF1, Ma and Ptashne, *Cell* 51:113–119 (1987); Courey and Tjian (1988); Mermod et al., *Cell* 58:741–753 (1989)).

One of the most efficient activator domains known is contained in the carboxyl-terminal 100 amino acids of the Herpes Simplex Virus (HSV) virion protein 16 (VP16; Sadowski et al., *Nature* 335:563–564 (1988); Triezenberg et al., *Genes & Dev.* 2:718–729 (1988)). VP16, also known as Vmw65 or alpha-gene trans-inducing factor, is a structural protein of HSV which activates transcription of the immediate early promoters of the virus, including those for ICP0 and ICP4 (Campbell et al., *J. Mol. Biol.* 180:1–19 (1984); Kristie and Roizman, *Proc. Natl. Acad. Sci., USA* 81:4065–4069 (1984); Pellet et al., *Proc. Natl. Acad. Sci., USA* 82:5870–5874 (1985)). Although VP16 specifically activates promoters containing the so called TAATGARAT element, the specificity is endowed by a cellular DNA binding protein(s) which is complexed with the amino terminal domains(s) of VP16 (McKnight et al., *Proc. Natl. Acad. Sci., USA* 84:7061–7065 (1987); Preston et al., *Cell* 52:425–434 (1988)).

The present invention provides novel hybrid/chimeric transactivating proteins comprising a functional portion of a DNA binding protein and a functional portion of a transcriptional activator protein. The hybric/chimeric transactivating proteins of the invention offer a variety of advantages, including the specific activation of expression of hypoxia-inducible genes containing hypoxia responsive elements (HREs), thereby achieving exceptionally high levels of gene expression. Invention hybrid/chimeric transactivating proteins are capable of functioning in vertebrate cells and may include naturally occurring transcriptional transactivating proteins or domains of proteins from eukaryotic cells including vertebrate cells, viral transactivating proteins or any synthetic amino acid sequence that is able to stimulate transcription from a vertebrate promoter. Examples of such transactivating proteins include, but are not limited to, the lymphoid specific transcription factor identified by Muller et al. (*Nature* 336:544–551 (1988)), the fos protein (Lucibello et al., *Oncogene* 3:43–52 (1988)); v-jun protein (Bos et al., *Cell* 52:705–712 (1988)); factor EF-C (Ostapchuk et al., *Mol. Cell. Biol.* 9:2787–2797 (1989)); HIV-1 tat protein (Arya et al., *Science* 229:69–73 (1985)), the papillomavirus E2 protein (Lambert et al., *J. Virol.* 63:3151–3154 (1989)) the adenovirus E1A protein (reviewed in Flint and Shenk, *Ann. Rev. Genet.* (1989), heat shock factors (HSF1 and HSF2) (Rabindran, et al., *PNAS* 88:6906–6910 (1991)); the p53 protein (Levine, *Cell* 88:323–331 (1997), Ko and Prives, *Genes Dev.* 10:1054–1072 (1996)); Sp1 (Kadonaga, et al. *Cell* 51:1079–1090 (1987)); AP1 (Lee, et al., *Nature* 325:368–372 (1987)); CTF/NF1 (Mermod, et al., *Cell* 58:741–753 (1989)), E2F1 (Neuman, et al., *Gene* 173: 163–169 (1996)); HAP1 (Pfeifer, et al., *Cell* 56: 291–301 (1989)); HAP2 (Pinkham, et al., *Mol. Cell. Biol.* 7:578–585 (1987)); MCM1 (Passmore, et al., *J. Mol. Biol.* 204:593–606 (1988); PHO2 (Sengstag, and Hinnen, NAR 15:233–246 (1987)); and GAL11 (Suzuki et al., *Mol. Cell. Biol.* 8:4991–4999 (1988)). In preferred embodiments of the invention, the transactivating protein is Herpes simplex virus VP16 (Sadowski et al., *Nature* 335:563–564 (1988); Triezenberg et al., *Genes and Dev.* 2:718–729 (1988)), NFκB ((Schmitz and Baeuerle, *EMBO J.* 10:3805–3817 (1991); Schmitz, et al., *J. Biol. Chem.* 269:25613–25620 (1994); and Schmitz, et al., *J. Biol. Chem.* 270:15576–15584 (1995)), and yeast activators GAL4 and GCN4.

Of course, the skilled artisan will understand that transcriptional activation domains useful in the compositions and methods of this invention may also be synthetic, i.e., based on a sequence that is not contained within a known, naturally occurring protein. See, for example, Pollock and Gilman, *PNAS* 94:13388–13389 (1997), which teaches that transcriptional activation is an inherently flexible process in which there is little, if any, requirement for specific structures or stereospecific protein contacts. It also reviews the variety of different molecules that can function as transcriptional activators, including short peptide motifs (as small as eight amino acids), simple amphipathic helices and even mutagenized domains of proteins unrelated to transcriptional activation.

According to the invention, DNA sequences encoding the DNA binding protein and the transactivating protein are combined so as to preserve the respective binding and transactivating properties of each. In various embodiments of the invention, the DNA encoding the transactivating protein, or a portion thereof capable of activating transcription, may be inserted into DNA at a locus which does not completely disrupt the function of said DNA binding protein. Regions not required for function of DNA binding proteins or transcriptional transactivating proteins may be identified by any method known in the art, including analysis of mapped mutations as well as identification of regions lacking mapped mutations, which are presumably less sensitive to mutation than other, more functionally relevant portions of the molecule. The appropriate recombinant constructs may be produced using standard techniques in molecular biology, including those set forth in Maniatis (Molecular Cloning: A Laboratory Manual (Cold Spring Harbor, N.Y., Cold Spring Harbor Laboratory (1989)).

The recombinant DNA construct encoding the chimeric transactivator protein may be placed under the control of (i.e., operatively linked to) a suitable promoter and/or other expression control sequence. It may be desirable for the transactivator protein to be placed under the control of a constitutively active promoter sequence, although said transactivator protein may also be placed under the control of an inducible promoter, such as the metallothionine promoter (Brinster et al., *Nature* 296:39–42 (1982)) or a tissue specific promoter. Promoter sequences which may be used according to the invention include, but are not limited to, the SV40 early promoter region (Benoist and Chambon, *Nature* 290: 304–310 (1981)), the promoter contained in the long terminal repeat of Rous sarcoma virus (Yamamoto, et al., *Cell* 22:787–797 (1980)), the herpes thymidine kinase promoter (Wagner et al., *Proc. Natl. Acad. Sci., U.S.A.* 78:144–1445 (1981)), the human cytomegalovirus (CMV) immediate early promoter/enhancer (Boshart et al., *Cell* 41:521–530 (1985)), and the following animal transcriptional control regions, which exhibit tissue specificity and have been utilized in transgenic animals: elastase I gene control region which is active in pancreatic acinar cells (Swift et al., *Cell* 38:639–646 (1984); Ornitz et al., *Cold Spring Harbor Symp. Quant. Biol.* 50:399–409 (1986); MacDonald, *Hepatology* 7:425–515 (1987)); insulin gene control region which is active in pancreatic beta cells (Hanahan, *Nature* 315:115–122 (1985)), immunoglobulin gene control region which is active in lymphoid cells (Grosschedl et al., *Cell* 38:647–658 (1984); Adames et al., *Nature* 318:533–538 (1985); Alexander et al., *Mol. Cell. Biol.* 7:1436–1444 (1987)), mouse mammary tumor virus control region which is active in testicular, breast, lymphoid and mast cells (Leder et al., *Cell* 45:485–495 (1986)), albumin gene control region which is active in liver (Pinkert et al., *Genes and Devel.* 1:268–276 (1987)), alpha-fetoprotein gene control region which is active in liver (Krumlauf et al., *Mol. Cell. Biol.* 5:1639–1648 (1985); Hammer et al., *Science* 235:53–58 (1987)); alpha 1-antitrypsin gene control region which is active in the liver (Kelsey et al, *Genes and Devel.* 1:161–171 (1987)), beta-globin gene control region which is active in erythroid cells (Mogram et al., *Nature* 315:338–340 (1985); Kollias et al., *Cell* 46:89–94 (1986)); myelin basic protein gene control region which is active in oligodendrocyte cells in the brain (Readhead et al., *Cell* 48:703–712 (1987)); myosin light chain-2 gene control region which is active in skeletal muscle (Sani, *Nature* 314:283–286 (1985)), and gonadotropic releasing hormone gene control region which is active in the hypothalamus (Mason et al., *Science* 234: 1372–1378 (1986)). Of particular interest is the α-myosin heavy chain gene (Subramaniam, et al., *J. Biol. Chem.* 266:24613–24620, (1991)) and the myosin light chain-2 promoter (Henderson et al., *J. Biol. Chem.* 264:18142–18148 (1989) and Ruoqian-Shen et al., *Mol. Cell. Biol.* 11:1676–1685 (1991), both of which are active in cardiac muscle.

In one preferred specific embodiment of the invention, the chimeric transactivator protein is encoded by pcDNA3/HIF/VP16/Af12, constructed according to methods set forth in Example 1 and FIG. 1. In another preferred specific embodiment of the invention, the chimeric transactivator protein is encoded by pcDNA3/HIF/VP16/RI, which is identical to pcDNA3/HIF/VP16/Af12 except that the VP16 segment is inserted after codon 530 of the HIF-1α coding region.

According to the invention, the hybrid/chimeric transactivator proteins of the invention may be utilized to specifically regulate the expression of genes containing hypoxia responsive elements (HREs). These HREs correspond to a nucleic acid sequence recognized and bound by the DNA binding protein used as the backbone of the chimeric transactivator protein.

In general, the chimeric transactivator proteins of the invention may be used to selectively control the expression of genes of interest. For example, and not by way of limitation, the chimeric transactivator proteins of the invention may be placed under control of a constitutive promoter and may be used to constitutively increase the expression of a gene of interest associated with hypoxia responsive elements (HREs), for example, when it is desirable to produce a particular gene product in quantity in a cell culture or in a transgenic animal. Alternatively, the transactivator protein may be placed under the control of a tissue-specific promoter so that the gene of interest is expressed in a particular tissue. In alternative embodiments of the invention, the chimeric transactivator function is inducible, so that the expression of a gene of interest, via hypoxia responsive elements (HREs), may be selectively increased or decreased. For reviews of conditional and inducible transgene expression, see Fishman, *Circ. Res.*, 82:837–844 (1998) and Fishman, *Trends Cardiovasc. Med.*, 5:211–217 (1995).

The chimeric transactivating proteins possess the advantageous property of binding specifically to responsive elements homologous to DNA sequences recognized by the chimeric protein's DNA binding protein backbone.

Vectors: Examples of vectors are viruses, such as adenoviruses, adeno-associated viruses (AAV), lentiviruses, herpes viruses, positive strand RNA viruses, vaccinia viruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

Polynucleotides/transgenes are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

The skilled artisan will recognize that when expression from the vector is desired, the polynucleotides/transgenes are operatively linked to expression control sequences. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Similarly, alternative codons, encoding the same amino acid, can be substituted for coding sequences of the human HIF-1α, EPAS1 or HLF polypeptide in order to enhance transcription (e.g., the codon preference of the host cell can be adopted, the presence of G-C rich domains can be reduced, and the like).

Preparations of invention polynucleotides encoding human HIF-1α, EPAS1 and HLF or another hypoxia inducible factor protein can be incorporated in a suitable vector for delivery into a individual's cells using methods that are known in the art. See, for example, Finkel and Epstein, *FASEB J.* 9:843–851 (1995); Feldman et al., *Cardiovascular Res.* 32:194–207 (1996).

In one embodiment, this invention provides compositions comprising a pharmaceutically acceptable carrier and nucleic acid molecules capable of expressing biologically active chimeric transactivator proteins. The chimeric transactivator proteins encoded by the nucleic acid molecules include a DNA binding domain from a hypoxia inducible factor protein and a protein domain capable of transcriptional activation. Such domain may be from either a naturally occurring or synthetic transcriptional activator molecule. The nucleic acid molecules within the composition are in a form suitable for delivery into cells in vivo or in vitro. A variety of such forms are well known in the art. Given the teachings set forth herein, the skilled artisan may select among various vectors and other expression/delivery elements depending on such factors as the site and route of administration and the desired level and duration of expression.

Naked DNA—Naked plasmid DNA can be introduced into muscle cells, for example, by direct injection into the tissue. (Wolff et al., *Science* 247:1465 (1989)).

DNA-Lipid Complexes—Lipid carriers can be associated with naked DNA (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, *Nature* 337:387 (1989)). Intravenous injection of cationic lipid-plasmid complexes into mice has been shown to result in expression of the DNA in lung (Brigham et al., *Am. J. Med. Sci.* 298:278 (1989)). See also, Osaka et al., *J. Pharm. Sci.* 85(6):612–618 (1996); San et al., *Human Gene Therapy* 4:781–788 (1993); Senior et al., *Biochemica et Biophysica Acta* 1070:173–179 (1991); Kabanov and Kabanov, *Bioconjugate Chem.* 6:7–20 (1995); Remy et al., *Bioconjugate Chem.* 5:647–654 (1994); Behr, J-P., *Bioconjugate Chem.* 5:382–389 (1994); Behr et al., *Proc. Natl. Acad. Sci., USA* 86:6982–6986 (1989); and Wyman et al., *Biochem.* 36:3008–3017 (1997).

Cationic lipids are known to those of ordinary skill in the art. Representative cationic lipids include those disclosed, for example, in U.S. Pat. No. 5,283,185; and PCT/US95/16174 (WO 96/18372), the disclosures of which are incorporated herein by reference. In a preferred embodiment, the cationic lipid is $N^4$-spermine cholesterol carbamate (GL-67) disclosed in WO 96/18372.

Adenovirus—Adenovirus-based vectors for the delivery of transgenes are well known in the art and may be obtained commercially or constructed by standard molecular biological methods. Recombinant adenoviral vectors containing exogenous genes for transfer are, generally, derived from adenovirus type 2 (Ad2) and adenovirus type 5 (Ad5). They may also be derived from other non-oncogenic scrotypes. See, for example, Horowitz, "Adenoviridae and their Replication" in *VIROLOGY*, 2d ed., Fields et al. Eds., Raven Press Ltd., New York, 1990, incorporated herein by reference.

The adenoviral vectors of the present invention are incapable of replicating, have minimal viral gene expression and are capable of expressing a transgene in target cells. Adenoviral vectors are generally rendered replication-defective by deletion of the E1 region genes. The replication-defective vectors maybe produced in the 293 cell line (ATCC CRL 1573), a human embryonic kidney cell line expressing E1 functions. The deleted E1 region may be replaced by the transgene of interest under the control of an adenoviral or non-adenoviral promoter. The transgene may also be placed in other regions of the adenovirus genome. See, Graham et al., "Adenovirus-based Expression Vectors and Recombinant Vaccines" in *VACCINES: NEW APPROACHES to IMMUNOLOGICAL PROBLEMS* pp 363–390, Ellis, Ed., Butterworth-Heinemann, Boston, (1992) for a review of the production of replication-defective adenoviral vectors, also incorporated herein by reference.

Skilled artisans are also aware that other non-essential regions of the adenovirus can be deleted or repositioned within the viral genome to provide an adenoviral vector suitable for delivery of a transgene in accordance with the present invention. For example, PCT/US93/11667 (WO 94/12649) and U.S. Pat. No. 5,670,488, incorporated herein by reference, discloses that some or all of the E1 and E3 regions may be deleted, and non-essential open reading frames (ORFs) of E4 can also be deleted. Other representative adenoviral vectors are disclosed, for example, by Rich et al., *Human Gene Therapy* 4:461 (1993); Brody et al., *Ann. NY Acad. Sci.* 716:90 (1994); Wilson, *N. Eng. J. Med.* 334:1185 (1996); Crystal, *Science* 270:404 (1995); O'Neal et al., *Hum. Mol. Genet.* 3:1497 (1994); and Graham et al., supra., incorporated herein by reference. In a preferred embodiment of the present invention, the adenoviral vector is an E1 deleted Ad2-based vector.

In the adenoviral vectors of the present invention, the polynucleotide/transgene is operably linked to expression control sequences, e.g., a promoter that directs expression of the transgene. As used herein, the phrase "operatively linked" refers to the functional relationship of a polynucleotide/transgene with regulatory and effector sequences of nucleotides, such as promoters, enhancers, transcriptional and translational stop sites, and other signal sequences. For example, operative linkage of a polynucleotide to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide.

Promoter regions include specific sequences that are sufficient for RNA polymerase recognition, binding and transcription initiation. Additionally, promoter regions include sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1a promoter or the Ad2 major late promoter (MLP). Similarly, those of ordinary skill in the art can construct adenoviral vectors utilizing endogenous or heterologous poly A addition signals.

As used herein "promoter" refers to the nucleotide sequences at the 5' end of a structural gene which direct the initiation of transcription. Promoter sequences are necessary, but not always sufficient, to drive the expression of a downstream gene. In general, eukaryotic promoters include a characteristic DNA sequence homologous to the consensus 5' TATA box about 10–30 bp 5' to the transcription start site (CAP site). Another promoter component, the CAAT box, is often found about 30–70 bp 5' to the TATA box.

As used herein "enhancer" refers to a eukaryotic promoter sequence element that appears to increase transcriptional efficiency in a manner relatively independent of position and orientation with respect to a nearby gene (Khoury and Gruss (1983) Cell 33:313–314). The ability of enhancer sequences to function upstream from, within or downstream from eukaryotic genes distinguishes them from classic promoter elements.

The viral and non-viral vectors of the present invention are useful for transferring a polynucleotide/transgene to a target cell. The target cell may be in vitro or in vivo. Use of invention vectors in vitro allows the transfer of a polynucleotide/transgene to a cultured cell and is useful for the recombinant production of the polynucleotide/transgene product. In vitro methods are also useful in ex vivo gene therapy methods, in which a transgene is introduced into cells in vitro and the cells are then implanted into an individual. The skilled artisan will recognize that in employing such techniques, the transgene may be introduced into freshly isolated cells or cultured cells. Furthermore, the transgene-containing cells may be implanted immediately after introduction of the transgene or may be cultured prior to implantation.

The vectors of this invention find use in a variety of ex vivo gene therapy methods useful for prevention or treatment of ischemia and other hypoxia-associated disorders. For example, it has been reported that transplantation of cultured cardiomyocytes into myocardial scar tissue may prevent heart failure (Ren-Ke Li et al., *Ann. Thorac. Surg.* 62:654–661 (1996). It has also been reported that various combinations of growth factors are capable of inducing cardiogenesis in cells of non-cardiac lineages (see PCT/US97/14229). Given the teachings contained herein, the skilled artisan will understand that introduction of a nucleic acid molecule capable of expressing a chimeric transactivator protein according to this invention into target cells prior to implantation in vivo may provide additional advantages to cellular therapy methods in at least two ways. First, the cells may serve as a transport vehicle for the expression construct, resulting in site-directed delivery of the chimeric transactivator protein in any region of the body in which the cells are transplanted. Second, the expression of a chimeric transactivator protein in the implanted cells may aid their survival after implantation, either by allowing them to more easily adapt to any hypoxic conditions which may be present after implant, and/or by stimulating blood vessel development in the region of implantation.

Use of invention vectors to deliver a polynucleotide/transgene to a cell in vivo is useful for the treatment of various disorders, for example, in the case of hypoxia-associated disorders such as ischemic heart disease, to a cell in which HIF-1α is absent, insufficient or nonfunctional. Thus, in further embodiments, this invention provides methods for increasing the expression of hypoxia-inducible genes in target cells of a subject in which such increased expression is desired by administering an effective amount of a composition comprising nucleic acid molecule encoding a biologically active chimeric transactivator protein according to this invention in form suitable for expression (e.g., operatively linked to expression control sequences). An "effective amount" refers to an amount which results in expression of biologically active chimeric transactivator protein at a level and for a period of time sufficient to alleviate one or more of the symptoms associated with a hypoxia-associated disorder. Such methods are useful to increase or sustain the expression of HIF-1α and hypoxia-inducible genes in tissues under hypoxic and normoxic conditions.

In related embodiments, the invention provides methods for treating, reducing and/or preventing hypoxia-associated tissue damage in a subject by in vivo or ex vivo administration of an effective amount of the nucleic acid molecules of this invention to cells in which expression of a biologically active chimeric transactivator protein is desired. The treatment and/or prevention of hypoxia-associated tissue damage may be manifested by a variety of physiological effects, including increased perfusion into a previously ischemic region of tissue. The methods of this invention find use in the treatment of such disorders as coronary artery disease and peripheral vascular disease, including critical limb ischemia.

In vivo administration of the compositions of this invention may be effected by a variety of routes including intramuscular, intravenous, intranasal, subctaneous, intubation, lavage and intra-arterial delivery. Such methods are well known to the skilled artisan. Likewise, the precise effective amount of the composition to be administered may be determined by the skilled artisan with consideration of factors such as the specific components of the composition to be administered, the route of administration, and the age, weight, extent of disease and physical condition of the subject being treated.

Also provided by this invention are vectors comprising a polynucleotide encoding human HIF-1α, EPAS1, HLF polypeptide and domains of other hypoxia, inducible factor proteins, adapted for expression in a bacterial cell, a yeast cell, an amphibian cell, an insect cell, a mammalian cell and other animal cells. The vectors additionally comprise the regulatory elements necessary for expression of the polynucleotide in the bacterial, yeast, amphibian, mammalian or animal cells so located relative to the polynucleotide as to permit expression thereof.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al., *Molecular Cloning, A Laboratory Manual 2d*

Ed. (Cold Spring Harbor, N.Y., 1989), or Ausubel et al., *Current Protocols in Molecular Biology* (Greene Assoc., Wiley Interscience, NY, N.Y., 1992). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention hybrid/chimeric transactivator (fusion) polypeptide.

This invention provides a transformed host cell that recombinantly expresses the invention hybrid/chimeric transactivator (fusion) polypeptides. Invention host cells have been transformed with recombinant nucleic acid molecules encoding chimeric transactivators comprising a DNA binding domain of a mammalian or non-mammalian hypoxia-inducible factor protein and a functional transcriptional activator domain of a transcriptional activator protein. An example is a mammalian cell comprising a plasmid adapted for expression in a mammalian cell. The plasmid contains a polynucleotide encoding a DNA binding domain of a mammalian or non-mammalian hypoxia-inducible factor protein and a functional transcriptional activator domain of a transcriptional activator protein and the regulatory elements necessary for expression of the invention hybrid/chimeric transactivator (fusion) polypeptides.

Appropriate host cells include bacteria, archebacteria, fungi, especially yeast, plant cells, insect cells and animal cells, especially mammalian cells. Of particular interest are *E. coli, B. subtilis, Saccharomyces cerevisiae,* SF9 cells, C129 cells, 293 cells, *Neurospora,* and CHO cells, COS cells, HeLa cells, and immortalized mammalian myeloid and lymphoid cell lines. Preferred replication systems include M13, ColE1, SV40, baculovirus, lambda, adenovirus, artificial chromosomes, and the like. A large number of transcription initiation and termination regulatory regions have been isolated and shown to be effective in the transcription and translation of heterologous proteins in the various hosts. Examples of these regions, methods of isolation, manner of manipulation, and the like, are known in the art. Under appropriate expression conditions, host cells can be used as a source of recombinantly produced invention hybrid/climeric transactivator (fusion) protein.

Nucleic acids (polynucleotides) encoding invention hybrid/chimeric transactivator (fusion) polypeptides may also be incorporated into the genome of recipient cells by recombination events. Other recombination-based methods such as nonhomologous recombinations or deletion of endogenous gene by homologous recombination, especially in pluripotent cells, may also be used.

Targeting invention vectors to target or host cells may be accomplished by linking a targeting molecule to the vector. A targeting molecule is any agent that is specific for a cell or tissue type of interest, including for example, a ligand, antibody, sugar, receptor, or other binding molecule. The ability of targeted vectors renders invention vectors particularly useful in the treatment of hypoxia-associated disorders.

Transfer of the polynucleotide/transgene to the target or host cells by invention vectors can be evaluated by measuring the level of the polynucleotide/transgene product in the target or host cell. The level of polynucleotide/transgene product in the target or host cell directly correlates with the efficiency of transfer of the polynucleotide/transgene by invention vectors.

Expression of the polynucleotide/transgene can be monitored by a variety of methods known in the art including, inter alia, immunological, histochemical and activity assays. Immunological procedures useful for in vitro detection of the hybrid/chimeric transactivator (fusion) polypeptide in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

For in vivo imaging methods, a detectable antibody can be administered to a subject, tissue or cell and the binding of the antibody to the polynucleotide/transgene product can be detected by imaging techniques well known in the art. Suitable imaging agents are known and include, for example, gamma-emitting radionuclides such as $^{111}$In, $^{99m}$Tc, $^{51}$Cr and the like, as well as paramagnetic metal ions, which are described in U.S. Pat. No. 4,647,447. The radionuclides permit the imaging of tissues by gamma scintillation photometry, positron emission tomography, single photon emission computed tomography and gamma camera whole body imaging, while paramagnetic metal ions permit visualization by magnetic resonance imaging.

The present invention provides isolated hybrid/chimeric transactivator (fusion) peptide(s), polypeptide(s) and/or protein(s) encoded by the invention nucleic acids. As used herein, the term "isolated" means a protein molecule free of cellular components and/or contaminants normally associated with a native in vivo environment. Invention polypeptides and/or proteins include any naturally occurring allelic variant, as well as recombinant forms thereof. Invention polypeptides can be isolated using various methods well known to a person of skill in the art.

The methods available for the isolation and purification of invention fusion proteins include, precipitation, gel filtration, and chromatographic methods including molecular sieve, ion-exchange, and affinity chromatography using e.g. HIF-1α-, EPAS1-, or HLF-specific antibodies or ligands. Other well-known methods are described in Deutscher et al., *Guide to Protein Purification: Methods in Enzymology Vol. 182,* (Academic Press, 1990). When the invention polypeptide to be purified is produced in a recombinant system, the recombinant expression vector may comprise additional sequences that encode additional amino-terminal or carboxy-terminal amino acids; these extra amino acids act as "tags" for immunoaffinity purification using immobilized antibodies or for affinity purification using immobilized ligands.

An example of the means for preparing the invention hybrid/chimeric transactivator (fusion) polypeptide(s) is to express invention polynucleotides in a suitable host cell, such as a bacterial cell, a yeast cell, an amphibian cell (i.e., oocyte), an insect cell (i.e., *drosophila*) or a mammalian cell, using methods well known in the art, and recovering the expressed polypeptide, again using well-known methods. Invention polypeptides can be isolated directly from cells that have been transformed with expression vectors, described herein in more detail. The invention hybrid/chimeric transactivator (fusion) polypeptide, biologically active fragments, and functional equivalents thereof can also be produced by chemical synthesis. As used herein, "biologically active fragment" refers to any portion of the polypeptide that can assemble into an active protein. Synthetic polypeptides can be produced using Applied Biosystems, Inc. Model 430A or 431A automatic peptide synthesizer (Foster City, Calif.) employing the chemistry provided by the manufacturer.

Modification of the invention nucleic acids, polynucleotides, polypeptides, peptides or proteins with the following phrases: "recombinantly expressed/produced", "isolated", or "substantially pure", encompasses nucleic acids, polynucleotides, polypeptides, peptides or proteins that have been produced in such form by the hand of man, and are thus separated from their native in vivo cellular environment. As a result of this human intervention, the recombinant nucleic acids, polynucleotides, polypeptides, peptides and proteins of the invention are useful in ways that the corresponding naturally occurring molecules are not, such as identification of selective drugs or compounds.

The present invention provides for non-human transgenic animals carrying transgenes encoding chimeric transactivator proteins. These transgenic animals may further comprise a gene of interest under the control of hypoxia responsive elements (HREs). In various embodiments of the invention, the transactivator protein may constitutively enhance the expression of the gene of interest. Alternatively, the transactivator protein may only enhance the expression of the gene of interest under certain conditions; for example, and not by way of limitation, by induction. The recombinant DNA molecules of the invention may be introduced into the genome of non-human animals using any method for generating transgenic animals known in the art.

The invention provides a transgenic non-human mammal that is capable of expressing nucleic acids encoding invention hybrid/chimeric transactivator (fusion) polypeptides.

Also provided is a transgenic non-human mammal capable of expressing nucleic acids encoding invention hybrid/chimeric transactivator (fusion) polypeptides so mutated as to be incapable of normal activity.

The present invention also provides a transgenic non-human mammal having a genome comprising antisense nucleic acids complementary to nucleic acids encoding invention hybrid/chimeric transactivator (fusion) polypeptides so placed as to be transcribed into antisense mRNA complementary to mRNA encoding invention fusion polypeptides, which hybridizes thereto and, thereby, reduces the translation thereof. The polynucleotide may additionally comprise an inducible promoter and/or tissue specific regulatory elements, so that expression can be induced, or restricted to specific cell types. Examples of non-human transgenic mammals are transgenic cows, sheep, goats, pigs, rabbits, rats and mice. Examples of tissue specificity-determining elements are the metallothionein promoter and the T7 promoter.

Animal model systems which elucidate the physiological and behavioral roles of invention polypeptides are produced by creating transgenic animals in which the expression of the polypeptide is altered using a variety of techniques. Examples of such techniques include the insertion of normal or mutant versions of nucleic acids encoding invention fusion polypeptides by microinjection, retroviral infection or other means well known to those skilled in the art, into appropriate fertilized embryos to produce a transgenic animal. See, for example, Carver, et al., Bio/Technology 11:1263–1270, 1993; Carver et al., Cytotechnology 9:77–84, 1992; Clark et al, Bio/Technology 7:487–492, 1989; Simons et al., Bio/Technology 6:179–183, 1988; Swanson et al., Bio/Technology 10:557–559, 1992; Velander et al., Proc. Natl. Acad. Sci., USA 89:12003–12007, 1992; Hammer et al., Nature 315:680–683, 1985; Krimpenfort et al., Bio/Technology 9:844–847, 1991; Ebert et al., Bio/Technology 9:835–838, 1991; Simons et al., Nature 328:530–532, 1987; Pittius et al., Proc. Natl. Acad. Sci., USA 85:5874–5878, 1988; Greenberg et al., Proc. Natl. Acad. Sci., USA 88:8327–8331, 1991; Whitelaw et al., Transg. Res. 1:3–13, 1991; Gordon et al., Bio/Technology 5:1183–1187, 1987; Grosveld et al., Cell 51:975–985, 1987; Brinster et al., Proc. Natl. Acad. Sci., USA 88:478–482, 1991; Brinster et al., Proc. Natl. Acad. Sci., USA 85:836–840, 1988; Brinster et al., Proc. Natl. Acad. Sci., USA 82:4438–4442, 1985; Al-Shawi et al., Mol. Cell. Biol. 10(3):1192–1198, 1990; Van Der Putten et al., Proc. Natl. Acad. Sci., USA 82:6148–6152, 1985; Thompson et al., Cell 56:313–321, 1989; Gordon et al., Science 214:1244–1246, 1981; and Hogan et al., Manipulating the Mouse Embryo: A Laboratory Manual (Cold Spring Harbor Laboratory, 1986).

Another technique, homologous recombination of mutant or normal versions of these genes with the native gene locus in transgenic animals, may be used to alter the regulation of expression or the stricture of the invention polypeptides (see, Capecchi et al., Science 244:1288, (1989); Zimmer et al., Nature 338:150, (1989)). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of invention fusion polypeptides.

In contrast to homologous recombination, microinjection adds genes to the host genome, without removing host genes. Microinjection can produce a transgenic animal that is capable of expressing both endogenous and exogenous polypeptides. Inducible promoters can be linked to the coding region of the nucleic acids to provide a means to regulate expression of the transgene. Tissue-specific regulatory elements can be linked to the coding region to permit tissue-specific expression of the transgene. Transgenic animal model systems are useful for in vivo screening of compounds for identification of ligands, i.e., agonists and antagonists, which activate or inhibit polypeptide responses.

This invention further provides a composition containing an acceptable carrier and any of an isolated, purified hybrid/chimeric transactivator (fusion) polypeptide, an active fragment thereof, or a purified, mature protein and active fragments thereof, alone or in combination with each other. These polypeptides or proteins can be recombinantly derived, chemically synthesized or purified. As used herein, the term "acceptable carrier" encompasses any of the standard pharmaceutical carriers, such as phosphate buffered saline solution, water and emulsions such as an oil/water or water/oil emulsion, and various types of wetting agents.

As used herein the term "effective amount" refers to an amount that alleviates the deficiency by the sustained production of biologically active chimeric human-viral transactivator protein in the cells of an individual. Sustained production of biologically active chimeric human-viral transactivator protein in individuals can be evaluated by the alleviation of the symptoms associated with hypoxia-associated disorders, for example ischemic heart disease, peripheral vascular disease, ischemic limb disease, and the like. The precise effective amount of vector to be used in the method of the present invention can be determined by one of ordinary skill in the art with consideration of, for example, individual differences in age, weight, extent of disease and condition of the individual.

The present invention further provides a method for providing biologically active chimeric human-viral transactivator protein to the cells of an individual with a hypoxia-associated disorder comprising introducing into a such individual an amount of invention vectors effective to infect and sustain expression of biologically active chimeric human-viral transactivator protein in cells in which the associated transcription factor is absent, insufficient or nonfunctional therein. Invention vectors may be delivered to the target cells as a pharmaceutical composition comprising the vector and a pharmaceutically acceptable carrier. The vector may be delivered to target cells by methods known in the art, for example, intravenous, intramuscular, intranasal, subcutaneous, intubation, lavage, and the like.

Accordingly, the present invention provides alternative approaches in which the expression of a range of potentially beneficial genes is induced following the expression of biologically active mammalian transcription factors.

HIF-1α was cloned by PCR from HeLa cell cDNA and inserted into the expression vector, pcDNA3 (Clontech, Palo Alto, Calif.; Invitrogen, San Diego, Calif.). In this plasmid, expression of the gene is controlled by the CMV promoter. Following confirmation of the structure of the construct by sequencing, it was tested in HeLa and 293 cells by cotransfection with reporter plasmids in which transcription of the luciferase gene is controlled by either the EPO promoter/enhancer or the VEGF promoter. Induction of HIF-1α activity was accomplished by treatment of the cells with wither $CoCl_2$ or desferrioxamine, both of which are known to induce HIF-1α activity by a mechanism similar to hypoxia. This assay confirmed that the HIF-1α protein was indeed active.

Two HIF-1α/VP16 hybrids were constructed, the first was truncated at amino acid 390 of HIF-1α, the second at amino acid 530. The transactivation domain of HSV VP16 (aa413–490) was then joined downstream. These proteins were tested by cotransfection into HeLa and 293 cells with either the EPO-luciferase or VEGF-luciferase reporter plasmids as described above. The results show that in both cell types, the levels of luciferase gene expression observed in cells cotransfected with the hybrids is higher (as much as 20–100×) than that obtained with HIF-1α even when exposed to induction by $CoCl_2$ or desferrioxamine. This result implies that the hybrid proteins are indeed active and that the VP16 domain confers strong transactivation activity even in the absence of induction (i.e., under normoxic conditions). This suggests that these hybrid/chimeric fusion proteins might be a viable therapeutic for ischemic heart disease.

The present invention is further illustrated by the following examples which in no way should be construed as being further limiting. The contents of all references cited throughout this application are hereby expressly incorporated by reference.

EXAMPLES

Example 1

Hybrid/Chimera Construction

A hybrid transcription factor (pcDNA3/HIF.VP-16.Afl2) composed of a DNA binding and dimerization domains from HIF-1α and the transactivation domain from herpes simplex virus VP16 (FIG. 1) was constructed to provide strong, constitutive activation of genes normally involved in the physiological adaptation to hypoxia. As is described below, we analyzed the effect of this HIF-1α/VP16 transcription factor on VEGF gene expression in vitro, and on neovascularization in a rabbit hindlimb ischemia model.

Recombinant Plasmids

Figure 2:
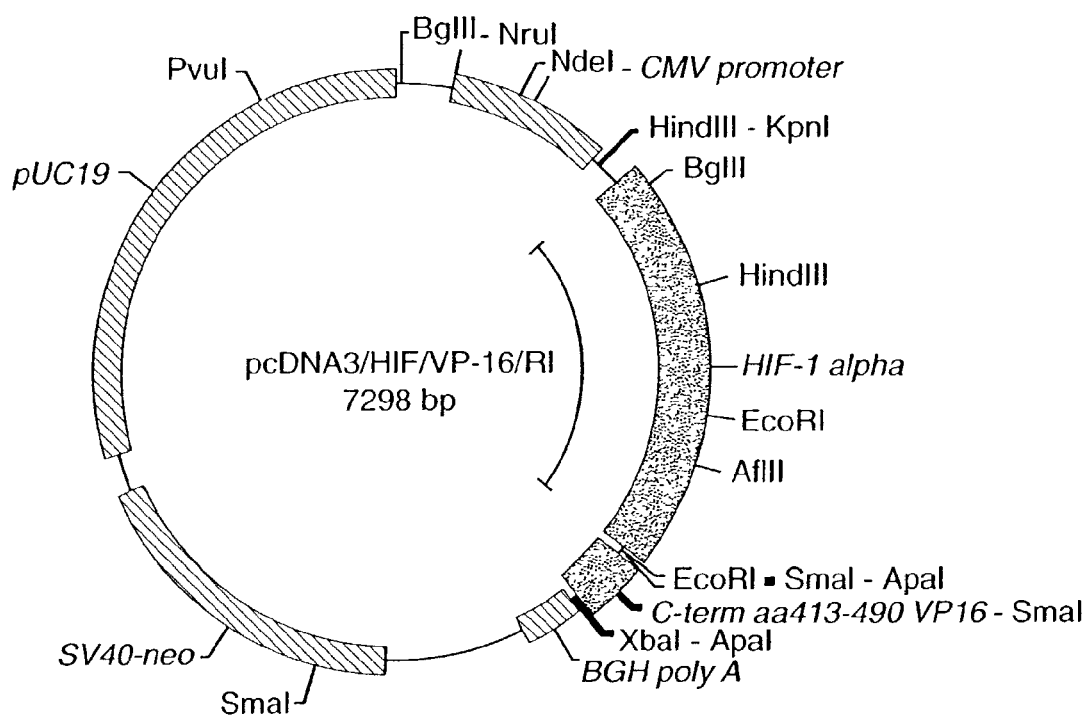
FIG. 2 shows a restriction map of hybrid construct pcDNA3/HIF/VP16/RI.

The full-length (aa1–826) HIF-1α gene was isolated by PCR (Advantage cDNA PCR Kit, Clontech, Palo Alto, Calif.) from a HeLa cell cDNA library (Clontech) using the primers set forth in SEQ ID NO's 1 and 2 and inserted between the KpnI and XbaI sites of the expression vector, pcDNA3 (Invitrogen, Carlsbad, Calif.). In this plasmid, gene expression is controlled by the cytomegalovirus (CMV) immediate early enhancer/promoter. The HIF-1α/VP-16 hybrid was constructed by truncating HIF-1α at aa390 (an Afl2 site) and then joining the transactivation domain of HSV VP-16 downstream. A VP16 fragment (aa 413–490) with Afl2 and XbaI ends was amplified by PCR using Vent polymerase (New England Biolabs, Beverly, Mass.) and the primers set forth in SEQ ID NO's 3 and 4 and this fragment was cloned into the appropriate sites of the pcDNA3/HIF-1α construct. A related construct (pcDNA3/HIF/VP-16/R1) was produced by truncating HIF-1α at aa530 by partial digestion with EcoR1 (FIG. 2). The integrity of all sequences generated by PCR was verified by DNA sequencing using an Applied Biosystems 377 DNA Sequencer. All cloning manipulations were carried out following standard procedures (Sambrook, J. et al., *Molecular Cloning, A Laboratory Manual 2d Ed.* (Cold Spring Harbor, N.Y., 1989)). Restriction enzymes and DNA-modifying enzymes were obtained from ether New England Biolabs or Life Technologies, Inc. (Gaithersburg, Md.)and used according to the maunfacturer's specifications. Plasmid DNAs were purified with kits obtained from Qiagen (Chatsworth, Calif.). The plasmid construct expressing human $VEGF_{165}$ (ph$VEGF_{165}$) has been described previously (Tsurumi, et al., *Circulation* 96:II-382–II-388 (1997)). Luciferase reporter plasmids (EPO-luc and VEGF-luc) were generously provided by Dr. H. Franklin Bunn (Brigham and Women's Hospital, Harvard Medical School).

Transient Transfections

HeLa cells were grown in Dulbecco's modified Eagles medium-high glucose (DME; Irvine Scientific, Santa Ana, Calif.) supplemented with 10% fetal bovine serum (FBS; JRH Biosciences, Lenexa, Kans.). For the luciferase reporter experiments, HeLa cells ($3\times10^5$ cells/60 mM dish) were transfected using the calcium phosphate ProFection kit (Promega, Madison, Wis.) according to manufacturer's instructions. Duplicate dishes were transfected with 5 µg of each plasmid (HIF-1α construct and either the EPO-luc (Blanchard, K. L., et al. *Mol. Cell. Biol.* 12:5373–85 (1992)) or the VEGF-luc (Levy, A. P., et al., *J. Biol. Chem.* 270: 13333–40 (1995)) reporter as well as pCMVβ (Clontech). At 24 hr post-transfection, one set of dishes was induced with 100 µM desferrioxamine. The cells were harvested 18 hr post-induction and luciferase activity was assayed (Promega). β-galactosidase activity in each sample was also determined using the Galacto-Light kit (Tropix, Bedford, Mass.) and these values were used to normalize the luciferase activity as a control for transfection efficiency.

Example 2

Activity of HIF-1α and HIF-1α/VP16 Chimeric/Hybrid Constructs in vitro

Figure 3:
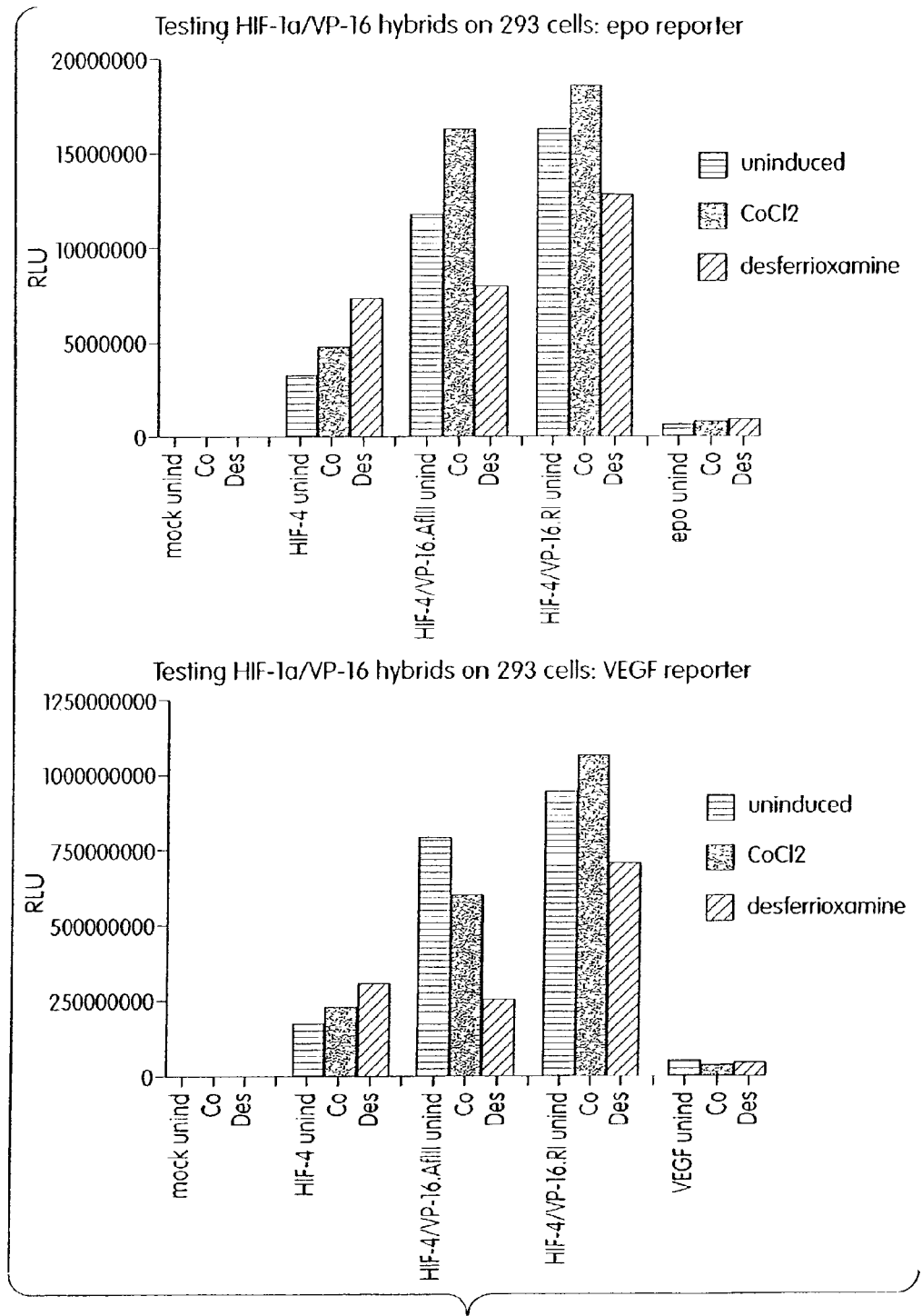
FIG. 3 shows the assay results testing the ability of the HIF-1α/VP16 hybrid constructs to activate EPO or VEGF gene expression in 293 cells.
Figure 4:
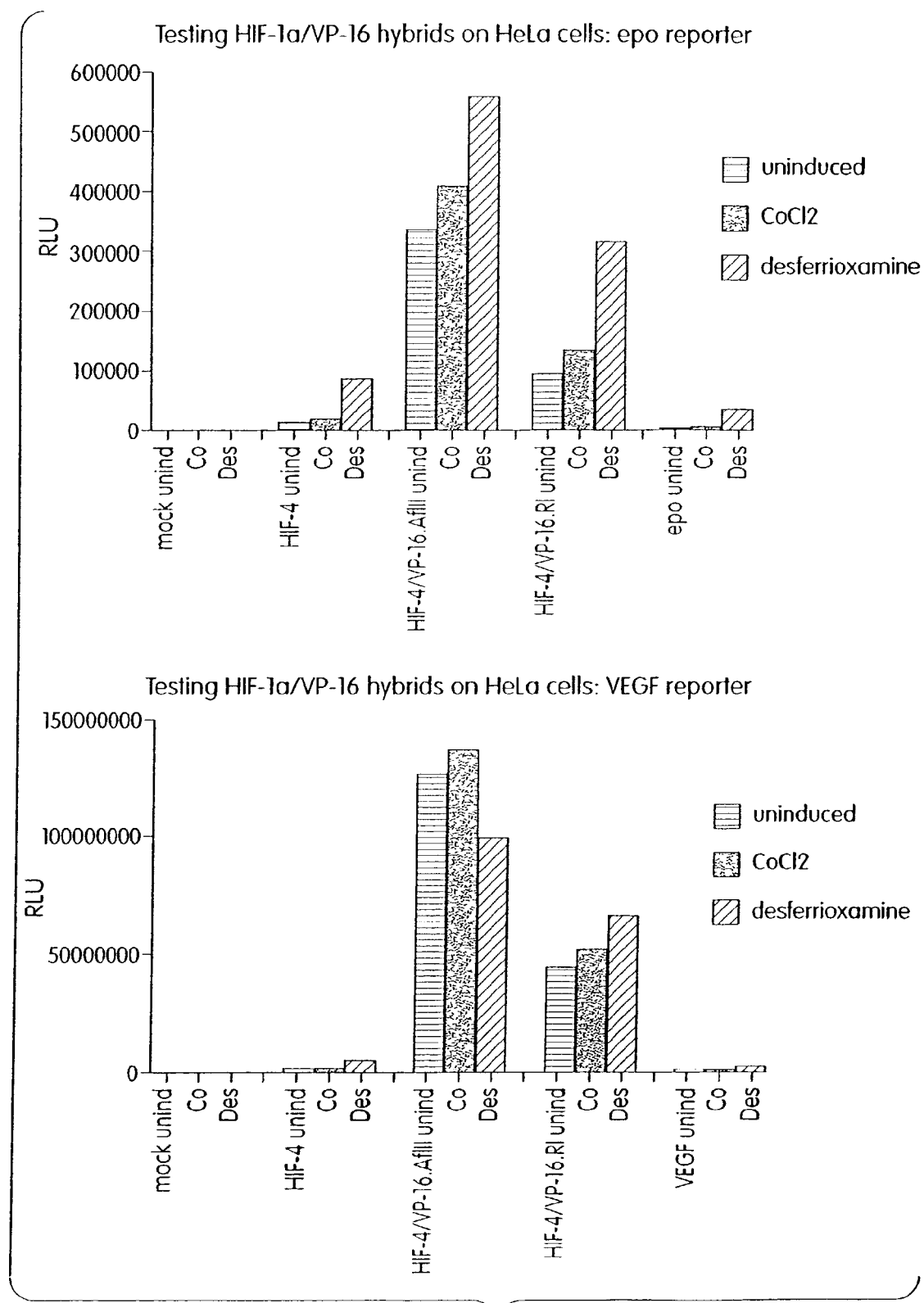
FIG. 4 shows the assay results testing the ability of the HIF-1α/VP16 hybrid constructs to activate EPO or VEGF gene expression in HeLa cells.
Figure 5:
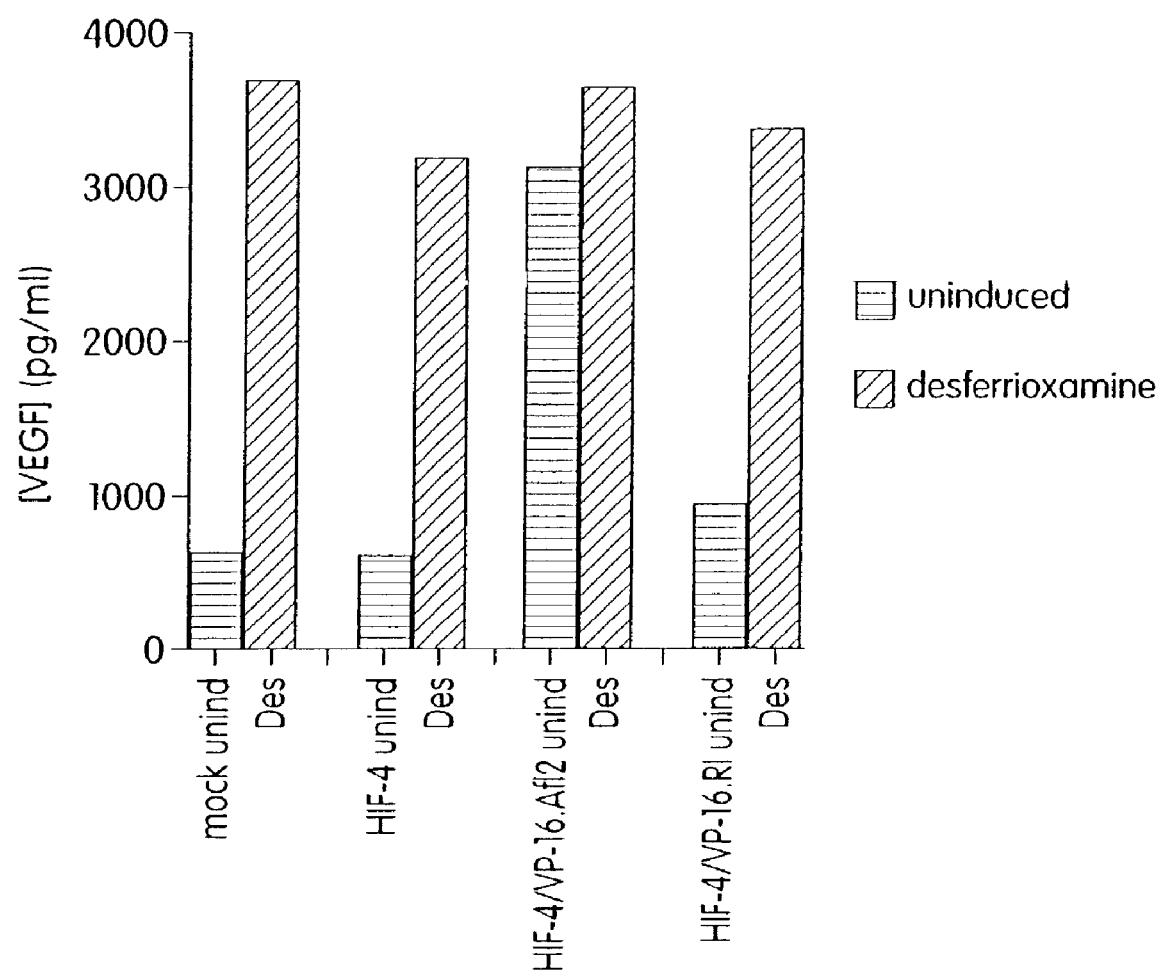
FIG. 5 shows assay results testing the ability of the HIF-1α/VP16 hybrid constructs to activate expression of an endogenous VEGF gene in HeLa cells.

The HIF-1α/VP16 hybrid constructs were tested for their ability to activate gene expression by cotransfection along with reporter plasmids into either 293 or HeLa cells (FIGS. 3 and 4, respectively). The reporter plasmids used in these experiments contained the luciferase gene under the transcriptional control of either the erythropoietin enhancer/promoter (Blanchard, K. L., et al., *Mol. Cell. Biol.* 12:5373–85 (1992)) or the VEGF promoter (Levy, A. P. et al., *J. Biol. Chem.* 270:13333–40 (1995)). (In FIGS. 3–5, pcDNA3/HIF/VP16.Af12 and pcDNA3/HIF/VP16.R1 are referred to as "HIF-4/VP-16.Af1II" and "HIF-4/VP-16.R1", respectively.)

Prior to transfection, cells were plated in 6 cm dishes at a density of $1 \times 10^6$ (239) or $2.5 \times 10^5$ (HeLa) cells per dish. Cells were co-transfected with the HIF-1α or HIF-1α/VP16 expression plasmids and a luciferase reporter plasmid containing either the EPO enhancer/promoter or the VEGF promoter.

Transfection was carried out by calcium phosphate precipitation using the ProFection™ kit (Promega, Madison, Wis.) using 5μg each of the HIF-1α/VP16 expressing constructs and the reporter plasmid per dish. At 24 hours post-transfection, cells were induced by adding fresh media containing either 100 μg/ml $CoCl_2$ or 100 μg/ml desferrioxamine. At 16 hours post-induction, the cells were harvested and the luciferase activity was measured using a luciferase assay kit (Promega) according to the manufacturer's instructions.

Figure 6:
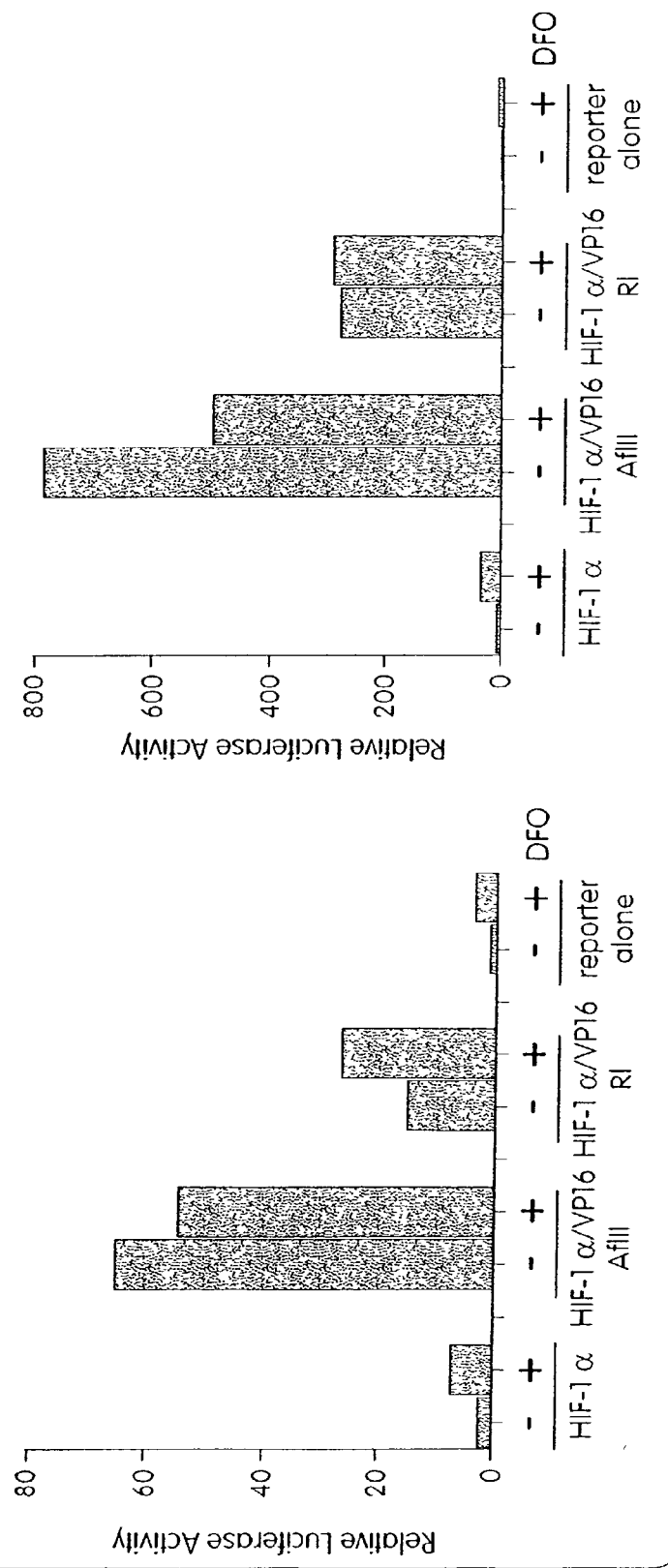
FIG. 6 shows results testing the ability of the HIF-1α/VP16 hybrid constructs to activate EPO (left) or VEGF (right) gene expression in 293 cells.

Induction of HIF-1 activity was simulated by treatment with desferrioxamine, an iron chelator, which acts via a mechanism similar to hypoxia. As was predicted for the HIF-1α/VP-16 hybrid transcription factor, luciferase expression was constitutive and not dependent of desferrioxamine induction. Luciferase expression in uninduced and desferrioxamine-treated cells was not significantly different. In contrast, luciferase activity in cells transfected with the full-length HIF-1α construct was increased 4–5 fold following treatment with desferrioxamine. Furthermore, transcriptional activation achieved by the HIF-1α/VP16 hybrid in uninduced cells was 10–20-fold higher than that observed in desferrioxamine-treated cells transfected with the full-length HIFα. Overall, levels of luciferase expression activated by HIF-1α were not much higher than the background levels attributable to endogenous HIF-1 activity in the HeLa cells. As shown in FIG. 6, subsequent studies have confirmed these findings. FIG. 6, left, shows luciferase activity produced using an EPO 3' enhancer-promoter-luciferase reporter construct. FIG. 6, right, shows luciferase activity produced using a VEGF promoter-luciferase reporter construct.

Example 3

VEGF Production in Response to the HIF-1α/VP16 Hybrid Constructs

To determine if the HIF-1α/VP16 hybrids were capable of activating expression of an endogenous VEGF gene, these constructs were transfected into HeLa cells and VEGF was assayed by ELISA. Prior to transfection, HeLa cells were plated in 6 cm dishes at a density of $2.5 \times 10^5$ cells per dish. The cells were transfected with 10 μg of the HIF-1α/VP16 hybrid plasmid DNA. At 24 hours post-transfection, cells in duplicate plates were either control (not-induced) or induced by adding fresh media containing 100 μg/ml desferrioxamine. At 40 hours post-induction, the media was harvested and assayed for VEGF by ELISA, (Quantikine™, R&D Systems, Minneapolis, Minn.) according to the manufacturer's instructions.

The results from this assay (FIG. 5) show that the hybrid HIF-1α/VP16/Af1II construct (truncated at amino acid 390 of HIF-1α) was able to activate expression of VEGF even in the absence of induction. The concentration of VEGF in the media from the HIF-1α/VP16/Af1II-transfected cells, however, was not higher than that observed in mock-transfected or HIF-1α-transfected cells with induction. This suggests that perhaps a maximum plateau level is achieved by the endogenous HIF-1α present in HeLa cells. The important observation, however, is that this level can be achieved with the HIF-1α/VP16/Af1II hybrid in the absence of induction.

The same result was not achieved with the second hybrid construct, HIF-1α/VP16/R1 (truncated at amino acid 530 of HIF-1α), although this construct had been active in the luciferase reporter assay. Additional in vitro analyses have confirmed an apparent difference in activity between the two constructs. Specifically, the HIF-1α/VP16/Af12 construct (truncated at amino acid 390 of HIF-1α) is more active than the longer HIF-1α/VP16/R1 construct, both with respect to activation of transcription of luciferase reporter constructs and up-regulation of endogenous VEGF and EPO gene expression in HeLa and Hep3B cells. This difference in activity may be due to the presence in the longer construct of a portion of an "oxygen-dependent domain" of HIF-1α which is reported to confer instability under normoxic conditions, (see Huang et al., *PNAS* 95:7987–7992 (1998)).

In additional analyses of VEGF production, HeLa cells ($3 \times 10^5$ cells/60 mM dish) were transfected with Lipofectamine (Life Technologies, Inc; 3.7 μg DNA, 14 μl of Lipofectamine) in Opti-MEM media (Life Technologies, Inc.) for 17 hr. Seven hours later, one set of dishes was treated with 100 μM desferrioxamine. At 42 hr post-induction, the culture medium was harvested and the cells were lysed in 250 μl lysis buffer (0.5% NP-40, 1 mM EDTA, 50 mM Tris (pH 8.0), 120 mM NaCl, 100 μM PMSF, 0.1 U/ml Aprotinin, 1 μM Pefabloc, 5 μg/ml Leupeptin). VEGF concentration was assayed as above and the total cell protein was analyzed using the Bio-Rad (Hercules, Calif.) protein assay. ELISA values were normalized to total cell protein.

Rat C6 glioma cells (American Type Culture Collection, Rockville Md.) were seeded onto 12-well culture plates 3 days before transfection and cultured with DME (Life Technologies, Inc) supplemented with 10% FBS (Sigma, St. Louis, Mo.). Transfection was performed essentially as described previously (Lee, E. R. et al. *Hum. Gene Ther.* 7:1701–1717 (1996)). Briefly, plasmid DNA was complexed with an equal volume of cationic lipid GL#67 to obtain a final concentration of 80:20 μM (DNA:lipid). Lipid/DNA complexes (400 μl/well, approximately $5 \times 10^5$ cells/well) were added to the cells in Opti-MEM media and incubated for 5 hrs. The complexes were then removed and cells returned to DME+10% FBS. The medium was replaced with fresh medium (1 ml/well) with or without desferrioxamine (100 μM) 24 hr after transfection. Twenty-four hours later, the medium was collected for analysis of VEGF production and the cells were lysed in 500 μl cell lysis buffer. VEGF production was assayed using an ELISA kit specific for mouse VEGF (R&D Systems) and values were normalized to total cell protein.

In both HeLa cells and C6 cells the HIF-1α/VP16 hybrid construct significantly enhanced production of VEGF in the absence of desferrioxamine treatment. In HeLa cells, VEGF production in HIF-1α/VP16-transfected cells was further enhanced by desferrioxamine, but in C6 cells, no difference was observed. Background levels of VEGF expression were much higher in HeLa than in the C6 cells. A much greater effect of the HIF-1α/VP16 hybrid on the magnitude of VEGF expression was observed in the C6 cells (5-fold greater than untransfected or HIF-1α-transfected cells treated with desferrioxamine). In HeLa cells, VEGF production in uninduced HIF-1α/VP16-transfected cells was comparable to that in untransfected cells exposed to desferrioxamine. However, in both cell lines, the absolute amount of VEGF (2.3 pg/μg protein) produced in uninduced, HIF-1α/VP16-transfected cells was almost identical. These results suggest that the desferrioxamine-induced level of endogenous HIF-1α protein and/or HIF-1α activity is greater in HeLa than in C6 cells; this may be explained by a species or cell type-specific difference. Notably, the HIF-1α/VP16 hybrid, based on a human transcription factor, is able to activate the rat VEGF gene, suggesting conservation of HREs across species. Sequence analysis of the 5'-flanking region of the rat VEGF gene has revealed several potential HREs; the position of one of these is conserved between the rat and human genes. This element is located within a 28 bp region that is identical in the rat and human VEGF genes.

Example 4

Analysis of the HIF-1α/VP16 Hybrid Transcription Factor in the Rabbit Hindlimb Ischemia Model A. Serum VEGF Level Naked plasmid DNA encoding either the HIF-1α/VP16 hybrid gene (pHIF-1α/VP16) or human $VEGF_{165}$ (ph-$VEGF_{165}$) was administered by injection into the medial large, adductor and semimembranous muscles of rabbits in which the femoral artery had been excised to induce hindlimb ischemia. Serum VEGF levels were assayed by an ELISA assay prepared against human VEGF. Accordingly, this assay as applied to the HIF-1α/VP16-treated group may not be quantitative as the endogenous rabbit protein is produced in these animals. However, the kinetics and persistance of VEGF expression may be compared among the groups. Before treatment serum VEGF levels were almost undetectable and similar for each group. However, at 3 days post-administration, the VEGF levels increased to 10.5 (±3.9) pg/ml in the $phVEGF_{165}$-transfected animals and to 26.3 (±4.6) pg/ml in the pHIF-1α/VP16-treated group. The VEGF levels in the pHIF-1α/VP16-treated animals were still high, yet reduced (14.9±3.0 pg/ml) at 5 days after treatment. In contrast, at 5 days, serum VEGF was undetectable in the animals treated with $phVEGF_{165}$. VEGF was not detected in the control (pCMVβ-treated) group either before or at 3 and 5 days after treatment. Though VEGF protein levels had decreased by five days, expression of both transgenes, analyzed by RT-PCR, persisted to 14 days post-administration.

B. Red Blood Cell Measurement

The red blood cell count, hematocrit and hemoglobin values before treatment (day 10) and 30 days after treatment (day 40) for the $phVEGF_{165}$, pHIF-1α/VP16, and control groups are shown in Table 1 below. There was no difference in red blood cell count and hemoglobin among the three groups either before or after treatment. Although the hematocrit appeared to increase in the pHIF-1α/VP16-treated animals, a similar increase was observed in the control group, suggesting that this result was not due to expression of the HIF-1α/VP16 hybrid transcription factor.

C. Lower-limb Calf Blood Pressure

At 10 days after induction of ischemia (immediately before plasmid injection), calf blood pressure ratio (ischemic/normal limb) was similar among the three groups ($phVEGF_{165}$=0.45±0.01, pHIF-1α/VP16=0.44±0.02, control=0.45±0.03; P=NS). By day 40 (30 days after transfection), the blood pressure ratio had improved among the three groups. The blood pressure ratio in the pHIF-1α/VP16-treated animals (0.93±0.02), however, was significantly higher (P<0.01) than in those that received $phVEGF_{165}$ (0.82±0.03)or the control group (0.69±0.02). The blood pressure ratio at day 40 was higher (P<0.01) in the $phVEGF_{165}$-treated group than in the controls.

D. Intravascular Doppler Guide Wire Measurements

Resting blood flow and maximal blood flow (papaverine-stimulated) in the ischemic limb were similar among the three groups at day 10. However, at day 40, the resting and papaverine-stimulated maximal blood flow in the pHIF-1α/VP16-transfected (41.6±3.1 mL/min and 111.2±5.7 mL/min, respectively) and $phVEGF_{165}$-transfected groups (42.2±3.9 mL/min and 88.7±7.4 mL/min, respectively) were significantly higher than that of the control group (28.7±1.5 mL/min and 65.3±3.8 mL/min, respectively). The resting flow was similar between pHIF-1α/VP16 and $phVEGF_{165}$-treated rabbits at day 40; however, the maximal flow was significantly higher (p<0.05) in the animals transfected with pHIF-1α/VP16 than in the $phVEGF_{165}$-treated group. Resting and maximal blood flow in the nonischemic limb were similar among the 3 groups at day 10 as well as day 40.

E. Effect of HIF-1α/VP16 and $VEGF_{165}$ on Collateral Vessel Development

Quantitative analysis of angiographically visible collateral vessels on the medial thigh was performed by determining vascular density. At baseline (day 10) before treatment, there was no significant difference in angiographic score among the $phVEGF_{165}$, pHIF-1α/VP16 and control groups (0.38±0.03, 0.42±0.01, 0.41±0.02, respectively; P=NS). By day 40, the angiographic scores in the pHIF-1α/VP16-treated (0.61±0.01) and in the $phVEGF_{165}$-treated (0.58±0.03) rabbits were significantly higher than that of the control group (0.51±0.05). There was no statistically significant difference in angiographic score at 40 days between pHIF-1α/VP16-treated and $phVEGF_{165}$-treated groups. The principal finding accounting for the increase in angiographic score observed in the animals that received pHIF-1α/VP16 and $phVEGF_{165}$ was enhancement in so-called mid-zone collateral vessels.

To further evaluate the effect of intramuscular HIF-1α/VP16 and VEGF gene therapy upon revascularization of the ischemic hindlimb, the medial thigh muscles of the ischemic limbs were histologically examined at day 40. Capillary densities observed in the muscles of the pHIF-1α/VP16-treated group (255±13/mm$^2$) and $phVEGF_{165}$-treated group (210±10/mm$^2$) were significantly higher than that of the control group (150±4/mm$^2$). In addition, the capillary density was higher (p<0.05) in the animals transfected with pHIFα/VP16 than in the $phVEGF_{165}$-treated animals. Moreover, the capillary/muscle fiber ratios of the pHIF-1α/VP16 and $phVEGF_{165}$-transfected rabbits (0.88±0.06 and 0.75±0.03, respectively) were significantly higher than the control (0.58±0.03; results not shown). Light microscopic signs of frank myonecrosis were not observed in either group.

Clinical Implications

Activation of VEGF gene expression by the HIF-1α/VP16 hybrid factor in vitro and in vivo suggests that the VP16 activation domain is able to interact with the accessory factors required for expression of the HIF-1 target gene in the cell types examined (human cervical epithelia, rat glioma, rabbit skeletal muscle). Thus, administration of the HIF-1α/VP16 hybrid via gene therapy may prove to be an effective treatment for ischemia associated with vascular disease. In this application, HIF-1α/VP16 may up-regulate a variety of genes, including VEGF. Therapeutic benefit may be achieved, not only as a result of stimulation of angiogenesis, but also through additional HIF-1-mediated local adaptations to low oxygen tension such as vasodilation and up-regulation of anaerobic metabolism. The administration of growth factors and/or the genes encoding them to enhance angiogenesis may be useful as a treatment for tissue ischemia in cases where conventional revascularization techniques are not feasible.

The enhanced potency observed with the HIF-1α/VP16 hybrid relative to $VEGF_{165}$ in vivo might be attributed to several factors. First, the levels of expression of VEGF promoted by HIF-1α/VP16 appreared to exceed that achieved with the $VEGF_{165}$ plasmid. Moreover, VEGF expression appeared to persist longer in the pHIF-1α/VP16-treated animals than in those that received $phVEGF_{165}$, since at 5 days post-administration, serum VEGF was detected in the former group but not in the latter.

F. Procedures

Intramuscular Gene Transfer

Twenty-nine rabbits were used to study the effect of intramuscular gene therapy on hindlimb ischemia. All protocols were approved by St. Elizabeth's Institutional Animal Care and Use Committee. Male New Zeland White rabbits (4.0 to 4.3 kg) (Pine Acre Rabbitry, Norton, Mass.) were anesthetized with a mixture of ketamine (50 mg/kg) and acepromazine (0.8 mg/kg) after premedication with xylazine (2 mg/kg). The surgical procedures have been previously described (Takeshita, S. et al., *Am. J. Physiol.* 93:662–670 (1994a)). Briefly, the femoral artery was completely excised from its proximal origin as a branch of the external iliac artery to the point distally where it bifurcates into the saphenous and popliteal arteries. All animals were closely monitored following surgery. Analgesia (0.25 mg/kg levophanol tartrate; Hoffmann-La Roche Inc., Nutley, N.J.) was administered subcutaneously for one day. Prophylactic antibiotics (enrofloxacin, Bayer Corporation, Shawnee Mission, Kans.) were also administered subcutaneously for a total of 5 days postoperatively.

An interval of 10 days was allowed for postoperative recovery, after which the rabbits were returned to the catheterization laboratory. Following completion of baseline measurements, four different sites in three major thigh muscles received direct injections with plasmid DNA or vehicle only (normal saline) with the use of a 3-ml syringe and a 25-gauge needle advanced through a small skin incision. For each injection, the tip of the needle was inserted typically to a depth of 3 to 5 mm in the medial large (two sites), adductor (one site), and semimembranous (one site) muscle. The detailed procedure for the muscle injection has been previously described (Tsurumi et al., *Circulation* 94:3281–3290 (1996)). This technique was used to administer 500 μg of pHIF-1α/VP16 (n=11), 500 μg of $phVEGF_{165}$ (n=10), or 500 μg of pCMVβ (n=8). One hundred and twenty five μg in 0.5 ml of normal saline was injected at each of four sites for a total of 500 μg/2.0 ml for each animal. After the completion of four injections, the skin was closed with 4-0 nylon sutures.

Immunoassay of Serum VEGF

For the first 6 rabbits in each group, blood samples were drawn from the central artery of the rabbit ear using a 23-gauge needle immediately before treatment as well as 3 and 5 days after plamid transfection. The blood sample was stored at 4° C. for 30 minutes and then centrifuged at 3,000 rpm for 15 minutes. Serum was frozen at −80° C. until assay of VEGF by ELISA (R&D Systems). The lower limit of detection of serum VEGF was 9.0 pg/mL. The assay was performed in duplicate for each sample. The intra-observer coefficient of variation was less than 8%.

Red Blood Cell, Hematocrit and Hemoglobin Measurement

Blood samples were drawn from the central artery of the rabbit car using a 23-gauge needle immediately before treatment (day 10) and at the day of sacrifice (day 40). The red blood cell, hematocrit and hemoglobin were measured by a commercially automatic detector (Sysmex alpha, Sysmex Corporation, Long Grove, Ill.).

Calf Blood Pressure Ratio

Calf blood pressure was measured in both hindlimbs using a Doppler flowmeter (Model 1050; Parks Medical Electronics, Aloha, Oreg.) immediately before treatment (day 10) as well as one month after initiation of the therapy (day 40). On each occasion, with rabbits under anesthesia, the hindlimbs were shaved and cleaned. The pulse of the posterior tibial artery was identified using a Doppler probe and the systolic blood pressure in both limbs was measured using standard techniques (Takeshita, S. et al., *Am. J. Physiol.* 93:662–670 (1994a)). The calf blood pressure ratio was defined for each rabbit as the ratio of systolic pressure of the ischemic limb to that of the normal limb.

In Vivo Doppler Flow Measurement

Blood flow was quantified in vivo before selective internal iliac angiography on days 10 and 40 with a 0.018-in Doppler guide wire (Cardiometrics, Inc., Mountain View, Calif.) as previously described (Banters, C. et al., *Am J Physiol.* 267:H1263–H1271 (1994)). The wire tip was positioned at the origin of the common iliac artery to the proximal segment of the internal iliac artery supplying the ischemic limb. Time average of the spectral peak velocity (APV) was recorded at rest and maximal APV was recorded after bolus injection of 2 mg of papaverine (Sigma, St. Louis, Mo.).

Doppler-derived blood flow ($Q_D$) was calculated as $Q_D = (\pi d^2/4)(0.5 \times APV)$, where d is vessel diameter, and APV is time average of the spectral peak velocity. The luminal diameter of the iliac artery was determined angiographically with an automated edge-detection system that has been validated previously in vivo. The vascular diameter was measured at the site of the Doppler sample volume (5 mm distal to the wire tip). Cross-sectional area was calculated assuming a circular lumen. The mean velocity was estimated as 0.5×APV by assuming a time-averaged parabolic velocity profile across the vessel. The Doppler-derived flow calculated in this fashion has been shown to correlate with flow measurements determined by electromagnetic flowmeters both in vitro and in vivo (Tsurumi et al., *Circulation* 94:3281–3290 (1996)). Because 2 mg of papaverine had no effect on vessel diameter (Ku, D. D., et al., *Am. J. Physiol.* 265:H586–H592 (1993)), the diameter measurements were used to calculate both rest and maximum flow.

Selective Angiography

Selective internal iliac angiography was performed as previously described (Takeshita, S. et al. *Am. J. Physiol.* 93:662–670 (1994a)). The tip of the catheter was positioned in the internal iliac artery at the level of interspace between the seventh lumbar and the first sacral vertebrae. A total of 5 ml of nonionic contrast media (Isovue-370; Squibb Diagnostics, New Brunswick, N.J.) was injected with an automated angiographic injector at a flow rate of 1 ml/s through a 3F infustion catheter (Tracker-18; Target Therapeutics, Fremont, Calif.) positioned in the internal iliac artery. Serial images of the ischemic hindlimb were then recorded on 105-mm spot film at a rate of one film per second for at least 10 seconds. After completion of angiography, the catheter was removed and the wound was closed.

Quantitative angiographic analysis of collateral vessel development was performed using a grid overlay comprised of 2.5-mm-diameter circles arranged in rows spaced 5 mm apart. This overlay was placed over the medial thigh area of the 4-s angiogram. The total number of grid intersections in the medial thigh area, as well as the total number of intersections crossed by a contrast-opacified artery, were counted in a single blind fashion. An angiographic score was calculated for each film as the ratio of grid intersections crossed by opacified arteries divided by the total number of grid intersections in the medial thigh.

Capillary Density

Vascular density was evaluated at the microvascular level using light microscopic sections taken from the ischemic hindlimbs. Tissue specimens were -obtained as transverse sections from the adductor muscle and semimembranous muscle of the ischemic limb when the animals were sacrificed. Muscle samples were embedded in OCT compound (Miles, Elkhart, Ind.), snap-frozen in liquid nitrogen, and cut into 5-um-thick sections. Tissue sections were stained for alkaline phosphatase with an indoxyl-tetrazolium method to detect capillary endothelial cells as previously described (Ziada, A. M., et al., *Cardiovasc. Res.* 18:724–732 (1984)) and then were counterstained with eosin. A total of 20 different fields from the two muscles were randomly selected, and the number of capillaries and myofibers counted under a 20x objective. The capillary density (capillaries/mm$^2$) and the capillary-to-myocyte ration were then determined.

Example 5

HIF-1α/VP16 Recombinant Adenoviruses

As an alternative to naked DNA, adenoviral vectors were constructed carrying the HIF-1α-based genetic construct, as described below.

Two HIF-1α/VP16 hybrids were cloned into a previral plasmid vector (CMV promotor, SV40 pA, p1X-; called "empty vector" (EV)—obtained originally from R. Doll). As is described above, these two hybrid proteins contain the DNA-binding and dimerization domains from HIF-1α (the first is truncated at aa390 of HIF-1α at an AFl11 site; the second is truncated at aa 530 at EcoR1 site) and the transactivation domain from Herpes Simplex Virus VP-16 protein.

Shuttle vector EV/HIF-1α/VP-16.Afl11 was linearized with BstB1 and shuttle vector EV/HIF-1α/VP16.R1 was linearized with BamH1. 15 µg of DNA of each vector was digested for 4 hours, then purified twice by phenol/chloroform extraction and ethanol precipitation. Pellets were resuspended in 50 µl of 0.1xTE and used for transfection (2 µl of each digested DNA were run on a gel prior to transfection).

Preparation of Viral Backbone DNA

5 µg of Ad2CMVBgal-6 DNA were digested with PshAI and SnaBI at 37° C. for about 24 hours, and 1/10 of the reaction was run on 0.8% Agarose/TBE gel to check the completion of digestion. The rest of the reaction was used for transfection.

The Ad2CMVBgal-6 backbone is the same as that of the vector described in the Example of U.S. Pat. No. 5,707,618, incorporated herein by reference in its entirety, except that it contains the B-gal gene inserted into the deleted E1 portion of the vector. Specifically, this vector is deleted for Ad E1, and E4 sequences are deleted from the ClaI site at 34077 to the TaqI site at 35597. The ORF6 sequence from 33178 to 34082 is inserted into the E4 region. The SV40 early polyA sequence is inserted adjacent to the ORF6, which also serves to prevent readthrough from the ORF6 gene into the L5 (fiber) sequences. Protein IX is repositioned from its original location in the virus genome into the E4-deleted region as a BamH1 fragment. The protein IX fragment contains its own promoter, and may be cloned into the vector in either direction. The construct is shown in FIG. 3 of the '618 patent.

Transfection

Transfection was conducted using the standard protocol from Promega's "Profection-Calcium Phosphate Transfection Kit," as follows.

Day One: Plate 293 cells on 60 mm dish at 1×10$^6$/dish and incubate at 37° C./5% CO$_2$ for 24 hours.

Day Two:
1. Four hours prior to the transfection, remove the medium from the cells and replace it with 4.5 ml of fresh growth medium.
2. Prepare the DNA and CaCl$_2$ mixture:

| | |
|---|---|
| 4 µg of viral backbone DNA (Ad2CMVBgal-6) | 120 µl |
| 10 µg of shuttle vector (EV + Afl11,EV + RI) | 48 µl |
| 2 M CaCl$_2$ | 37 µl |
| ddH$_2$O | 95 µl | in a 1.5 ml eppendorf tube and mix gentle. Leave mixture at room temperature for 15–30 minutes.

3. Precipitate DNA-CaCl$_2$ with 300 µl of 2xHBS and incubate at RT for 0.5 to 2 hours. Then add precipitated DNA to cells and incubate for 16–17 hours.

Day Three:
Change Medium.

Day Five:
Split cells from 60 mm dish to 100 mm dish.

Day Seven:
Split cells from 100 mm dish to 150 mm dish.

Day Nine:
Pick up 5 plagues of each transfection.

Day Eleven:
Pick up 12 more plagues from EV+RI and 10 more plagues from EV+Afl11. The plagues in 250 µl of growth medium were frozen and thawed 3 times and stored at −20° C.

Initial Screenings of Recombinant Adenoviruses
1. Infection

Day One:
Plate cells on 24 well plates at 1.4×10$^5$ cells/well.

Day Two:

Infect cells (about 40–50% confluent) with 200 µl of each plague at 37° C./5% $CO_2$ for 2 hours and then add 800 µl of growth medium. Replace cells in incubator and grow until CPE occurs.

Day Four:

Harvest one well of each plate when CPE is advanced.

Day Five:

Wash off CPE cells from 10 wells of EV+Af111 and 13 wells of EV+RI.

Day Eight:

Wash off remaining CPE cells.

Freeze/thaw CPE cell lysate 3 times.

2. Preparation of Viral DNA from CPE Cell Lysate

250 µl of CPE

250 µl of 2× proteinase K lysis buffer

40 µl of 10 mg/ml proteinase K

Cells were incubated at 37° C. for 3 hours and extracted 2 times with phenol/chloroform. Samples were precipitated with ethanol at 20° C. o/N and pellets were resuspended in 25 µl of dd$H_2O$. (Lysis buffer: 40 mM EDTA; 40 Mm Tris-HCl, PH 8; 2% SDS)

3. Viral DNA Digestion

Figure 7:
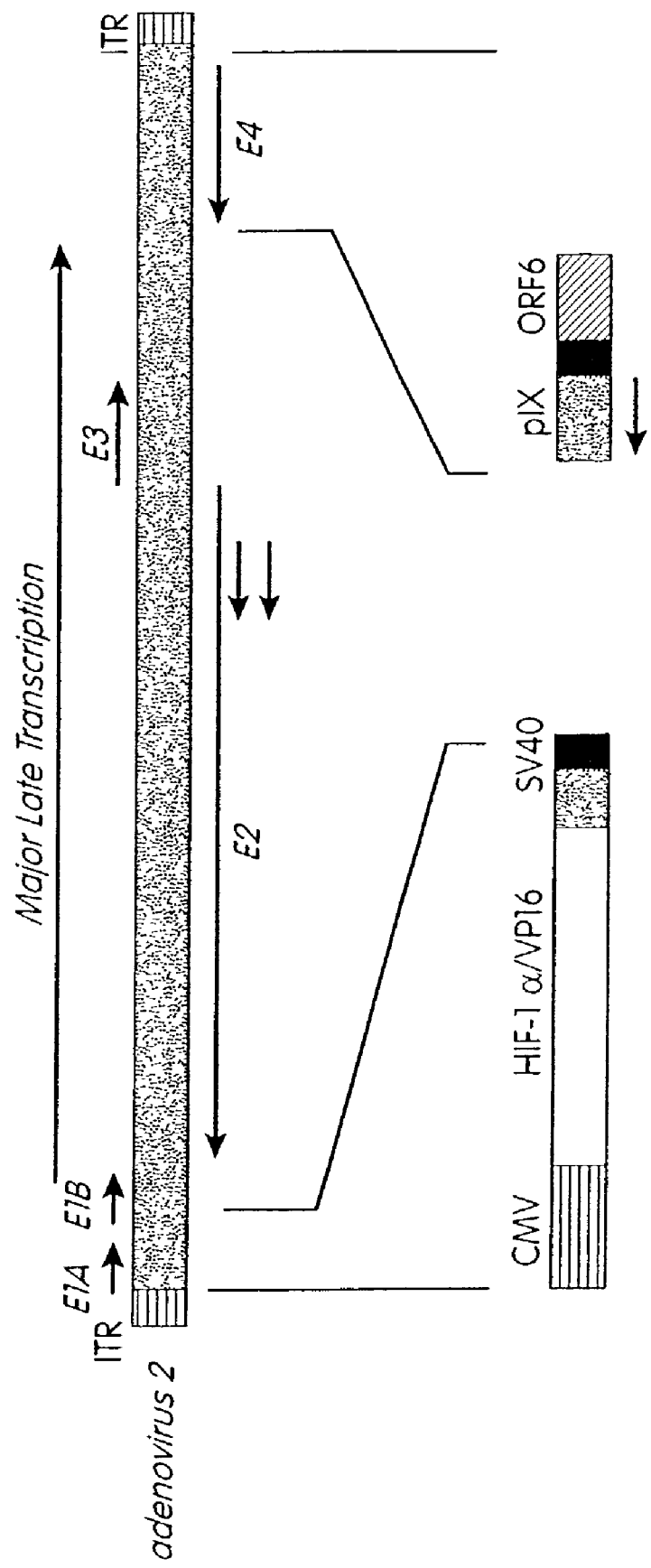
FIG. 7 shows a schematic of the adenoviral sequences contained with the HIF-1α/VP16 hybrid adenoviral vectors.

25 µl of DNA was digested with restriction enzyme BcII at 50° C. O/N and then separated on 0.8% agarose/TBE gel. All of the plagues were true recombinants. There was no background. A schematic of the adenoviral sequences contained within the HIF-1α/VP16 adenoviral vectors is shown in FIG. 7. This vector is identical to the Ad2CMVBgal-6 backbone except that the B-gal gene has been replaced with the HIF-1α/VP16 hybrid construct.

Example 6

HIF-1α/NFκB Hybrid Transactivators

Using techniques similar to those described in Example 1, we constructed a nucleic acid sequence encoding a chimeric transactivator protein comprising a DNA binding and dimerization domain from HIF-1α and a transactivation domain from NF-κB. Specifically, a DNA fragment coding for the-activation domain of the p65 subunit of NFκB (Schmitz, M. L. and Baeuerle, P. A., 1991 EMBO J. 10:3805–3817, Schmitz, M. L. et al., 1994 J. Biol. Chem. 269:25613–25620, Schmitz, M. L. et al., 1995, J. Biol. Chem. 270:15576–15584) was generated by PCR amplification of the DNA sequence (Advantage cDNA PCR kit, Clontech) from a HeLa cell cDNA library (Clontech). The DNA fragment was then inserted between the Af12 and XbaI sites of the pcDNA3/HIF-1α expression vector. This construct (pHIF-1α/NF-κB) therefore consists of aa 1–390 of HIF-1α and aa 407–551 of the NF-κB p65 subunit. The integrity of sequences generated by PCR was confirmed by DNA sequencing.

Figure 8:
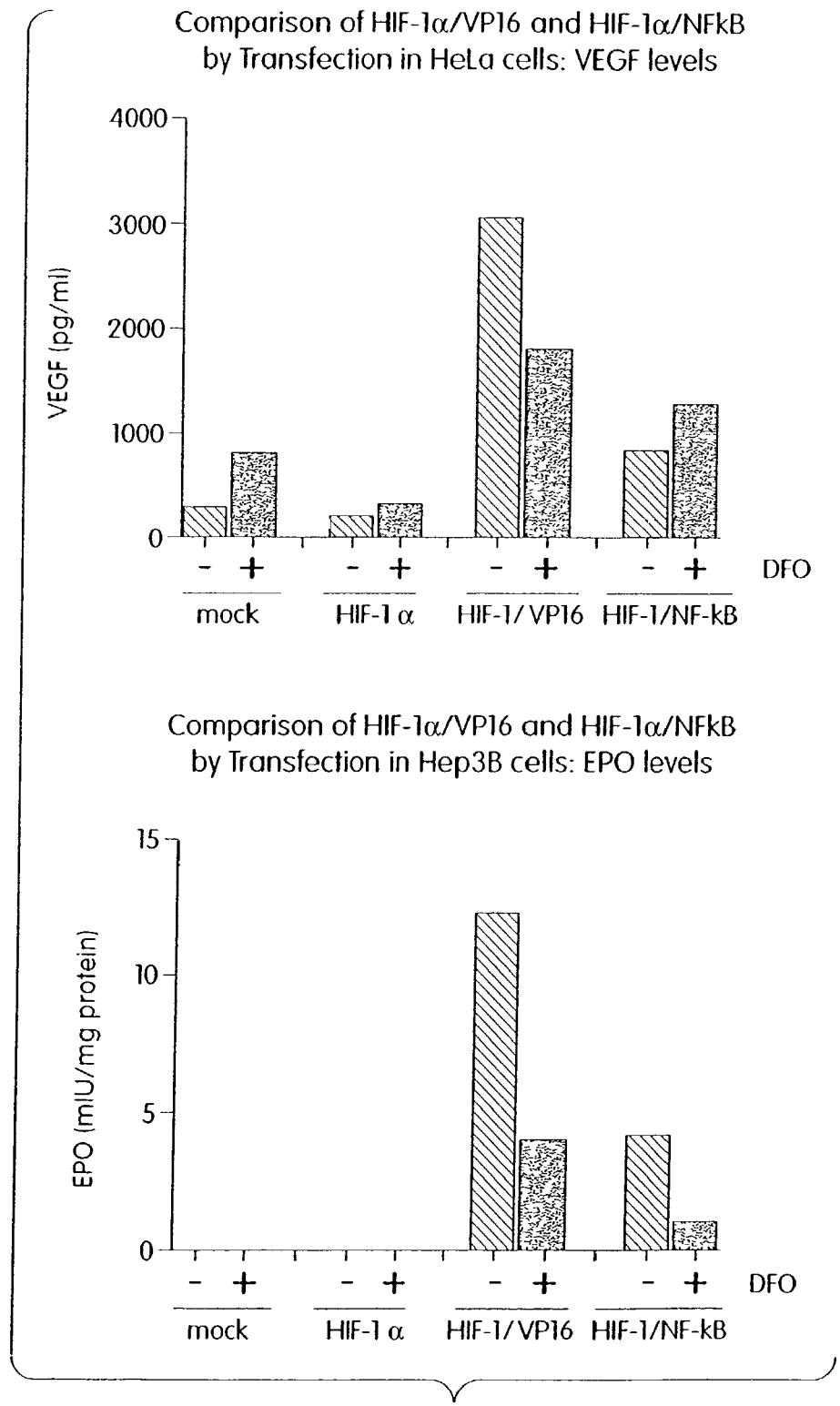
FIG. 8 shows assay results testing the ability of the HIF-1α/NFκB construct to activate expression of the endogenous VEGF gene in HeLa cells (top) and the endogenous EPO gene in Hep3B cells (bottom).

Initial in vitro experiments were performed to evaluate the ability of the HIF-1α/NF-κB hybrid to activate expression of the endogenous VEGF gene in HeLa cells. The pHIF-1α/NF-κB construct was transfected into duplicate plates of HeLa cells in parallel with the pHIF-1α/VP16 construct and pHIF-1α (full-length, wild-type HIF-1α gene) as a control, using methods similar to those described in Example 3. Twenty-four hours after transfection, one set of plates were exposed to desferrioxamine for induction of HIF-1α activity, the other set was left untreated. The media was harvested 48 hr after induction for assay of VEGF by ELISA (R & D Systems). As shown in FIG. 8 top, the pHIF-1α/NF-κB construct appears to be constitutively active, i.e. the level of VEGF detected in uninduced cells was relatively high, equal to that of induced, mock-transfected cells. However, the overall level of VEGF expression in cells transfected with the pHIF-1α/NF-κB construct was not as high as that observed in cells transfected with pHIF-1α/VP16.

A similar experiment was performed to evaluate up-regulation of erythropoietin (EPO) gene expression by pHIF-1α/NF-κB following transfection into Hep3B cells. As with VEGF, transfection of the cells with pHIF-1α/NF-κB results in expression of endogenous EPO in the absence of induction, however the levels of EPO are lower than those observed in cells transfected with pHIF-1α/VP16 (FIG. 8, bottom).

Although the invention has been described with reference to the disclosed embodiments, it should be understood that various modifications can be made without departing from the spirit of the invention. Accordingly, the invention is limited only by the claims which follow the References.

REFERENCES

Banai, S. et al., *Cardiovascular Res.* 28:1176–1179 (1994).

Blanchard, K. L. et al., *Molecular and Cellular Biology* 12(12): 5373–5385 (1992).

Blau, J. et al., *Molecular and Cellular Biology* 16(5): 2044–2055 (1996).

Bunn, H. F. et al., *Physiological Rev.* 76(3):839–885 (1996).

Cress, D. W. et al., *Science* 251:87–90 (1991).

Croston, G. E. et al., *Genes & Development* 6:2270–2281 (1992).

Ema, M. et al., *Proc. Natl. Acad. Sci., USA* 94:4273–4278 (1997).

Feldman, L. J. et al., *Cardiovascular Res.* 32:194–207 (1996).

Finkel, T. et al., *FASEB J.* 9:843–851 (1995).

Forsythe, J. A. et al., *Molecular and Cellular Biology* 16(9): 4604–4613 (1996).

Guillemin, K. et al., *Cell* 89(1):9–12 (1997).

Gupta, R. et al., *Nucleic Acids Research* 24(12):2324–2330 (1996).

Hashimoto, E. et al., *Am. J. Physiol.* 267(5 Part 1):H1948–H1954 (1994).

Huang, L. E. et al., *The Journal of Biological Chemistry* 271(50): 32253–32259 (1996).

International Publication Number WO 96/39426 (12, Dec. 1996).

International Publication Number WO 96/26742 (6, Sep. 1996).

Jiang, B-H et al., *The Journal of Biological Chemistry* 271(30):17771–17778 (1996).

Karck, M. et al., *Ann. Thorac. Surg.* 59:699–706 (1995).

Levy, A. P. et al., *The Journal of Biological Chemistry* 270(22): 13333–13340 (1995).

Li, H. et al., *The Journal of Biological Chemistry* 271(35): 21262–21267 (1996).

Maltepe, E. et al., *Nature* 386:403–407 (1997).

Ptashne, Mark, *Nature* 335:683–689 (1988).

Ptashne, Mark, *Nature Medicine* 3(10):1069–1072 (1997).

Ptashne, M. et al., *Nature* 386:569–577 (1997).

Pugh, C. W. et al., *The Journal of Biological Chemistry* 272(17):11205–11214 (1997).

Regier, J. L. et al., *Proc. Natl. Acad. Sci., USA* 90:883–887 (1993).

Rinsch, C. et al., *Human Gene Therapy* 8:1881–1889 (1997).
Semenza, G. L. et al., *Kidney International* 51:553–555 (1997).
Semenza, G. L. et al., *The Journal of Biological Chemistry* 269(38):23757–23763 (1994).
Simmen, K. A. et al., *Journal of Virology* 71(5):3886–3894 (1997).
Tian, H. et al., *Genes & Development* 11:72–82 (1996).
Wang, G. L. et al., *The Journal of Biological Chemistry* 270(3): 1230–1237 (1995).
Wang, G. L. et al., *Proc. Natl. Acad. Sci., USA* 90:4304–4308 (1993).
Wang, G. L. et al., *The Journal of Biological Chemistry* 268(29): 21513–21518 (1993).
Wang, G. L. et al., *Proc. Natl. Acad. Sci., USA* 92(12): 5510–5514 (1995).
Wiener, C. M. et al., *Biochemical and Biophysical Research Communications* 225:485–488 (1996).
Wood, S. M. et al., *The Journal of Biological Chemistry* 271(25): 15117–15123 (1996).
Wu, T. J. et al., *Molecular and Cellular Biology* 14(5): 3484–3493 (1994).

What is claimed is:

1. A nucleic acid molecule encoding a biologically active chimeric transactivator protein comprising:
    (a) the DNA binding domain of a human hypoxia inducible factor protein; and
    (b) a protein domain capable of transcriptional activation which is not derived from a hypoxia inducible factor protein.

2. The nucleic acid molecule according to claim 1, wherein said protein domain capable of transcriptional activation is derived from a protein selected from the group consisting of: HSV VP16, NFκB, a heat shock factor; p53; fos; v-jun; factor EF-C; HIV tat; HPV E2; Ad E1A; Sp1; AP1; CTF/NF1; E2F1; HAP1; HAP2; MCM1; PHO2; GAL4, GCN4, and GAL11.

3. The nucleic acid molecule according to claim 2, wherein said protein domain capable of transcriptional activation is a transcriptional activation domain from HSV VP16.

4. The nucleic acid molecule according to claim 2, wherein said protein domain capable of transcriptional activation is a transcriptional activation domain from NFκB.

---

SEQUENCE LISTING

```
<160> NUMBER OF SEQ ID NOS: 4

<210> SEQ ID NO 1
<211> LENGTH: 38
<212> TYPE: DNA
<213> ORGANISM: Homo sapiens

<400> SEQUENCE: 1
ggggtacctt ctcttctccg cgtgtggagg gagccagc                    38

<210> SEQ ID NO 2
<211> LENGTH: 37
<212> TYPE: DNA
<213> ORGANISM: Homo sapiens

<400> SEQUENCE: 2
gctctagagt gagccaccag tgtccaaaaa aaggatg                     37

<210> SEQ ID NO 3
<211> LENGTH: 33
<212> TYPE: DNA
<213> ORGANISM: Homo sapiens

<400> SEQUENCE: 3
cgtacgctta agccggaatt cccggggatc tgg                         33

<210> SEQ ID NO 4
<211> LENGTH: 32
<212> TYPE: DNA
<213> ORGANISM: Homo sapiens

<400> SEQUENCE: 4
cgctctagac tacccaccgt actcgtcaat tc                          32
```

5. An expression vector comprising the nucleic acid molecule according to any one of claims 1–4, operatively linked to an expression control sequence.

6. The expression vector according to claim 5, wherein said expression control sequence comprises an inducible promoter.

7. The expression vector according to claim 5, wherein said vector is an adenoviral vector.

8. The expression vector according to claim 7, wherein said expression control sequence comprises an inducible promoter.

9. An isolated host cell comprising the expression vector according to claim 5.

10. An isolated host cell comprising the expression vector according to claim 6.

11. An isolated host cell comprising the expression vector according claim 7.

12. An isolated host cell comprising the expression vector according claim 8.

13. A pharmaceutical composition comprising the expression vector according to claim 5 and a pharmaceutically acceptable carrier.

14. A pharmaceutical composition comprising the expression vector according to claim 6 and a pharmaceutically acceptable carrier.

15. A pharmaceutical composition comprising the expression vector according to claim 7 and a pharmaceutically acceptable carrier.

16. A pharmaceutical composition comprising the expression vector according to claim 8 and a pharmaceutically acceptable carrier.

17. A method for increasing the expression of a hypoxia-inducible gene in a mammalian cell, said method comprising the step of introducing into said mammalian cell in vitro the expression vector according to claim 5 so as to increase the expression of said hypoxia inducible gene in said cell.

18. A method for increasing the expression of a hypoxia-inducible gene in a mammalian cell, said method comprising the step of introducing into said mammalian cell in vitro the expression vector according to claim 6 so as to increase the expression of said hypoxia inducible gene in said cell.

19. A method for increasing the expression of a hypoxia-inducible gene in a mammalian cell, said method comprising the step of introducing into said mammalian cell in vitro the expression vector according to claim 7 so as to increase the expression of said hypoxia inducible gene in said cell.

20. A method for increasing the expression of a hypoxia-inducible gene in a mammalian cell, said method comprising the step of introducing into said mammalian cell in vitro the expression vector according to claim 8 so as to increase the expression of said hypoxia inducible gene in said cell.

21. A method for reducing ischemic tissue damage in a mammalian subject having a hypoxia-associated disorder comprising the step of administering at the site of said ischemic tissue damage in said subject an effective amount of the pharmaceutical composition according to claim 13.

22. A method for reducing ischemic tissue damage in a mammalian subject having a hypoxia-associated disorder comprising the step of administering at the site of said ischemic tissue damage in said subject an effective amount of the pharmaceutical composition according to claim 14.

23. A method for reducing ischemic tissue damage in a mammalian subject having a hypoxia-associated disorder comprising the step of administering at the site of said ischemic tissue damage in said subject an effective amount of the pharmaceutical composition according to claim 15.

24. A method for reducing ischemic tissue damage in a mammalian subject having a hypoxia-associated disorder comprising the step of administering at the site of said ischemic tissue damage in said subject an effective amount of the pharmaceutical composition according to claim 16.

* * * * *